US011278663B2

(12) United States Patent
Ramey et al.

(10) Patent No.: US 11,278,663 B2
(45) Date of Patent: Mar. 22, 2022

(54) CONNECTOR FOR MEDICATION DELIVERY SYSTEM

(71) Applicant: Kirk D. Ramey, Tallahassee, FL (US)

(72) Inventors: Kirk D. Ramey, Tallahassee, FL (US); Anthony David Smith, Rockwall, TX (US)

(*) Notice: Subject to any disclaimer, the term of this patent is extended or adjusted under 35 U.S.C. 154(b) by 31 days.

(21) Appl. No.: 14/967,343

(22) Filed: Dec. 13, 2015

(65) Prior Publication Data

US 2016/0271322 A1 Sep. 22, 2016

Related U.S. Application Data

(60) Provisional application No. 62/063,386, filed on Oct. 13, 2014.

(51) Int. Cl.
| | |
|---|---|
| *A61M 5/14* | (2006.01) |
| *A61M 5/142* | (2006.01) |
| *A61M 5/145* | (2006.01) |
| A61M 5/24 | (2006.01) |
| A61M 39/10 | (2006.01) |

(52) U.S. Cl.
CPC .......... *A61M 5/1413* (2013.01); *A61M 5/142* (2013.01); *A61M 5/14244* (2013.01); *A61M 5/14566* (2013.01); *A61M 5/14546* (2013.01); *A61M 2005/2474* (2013.01); *A61M 2039/1027* (2013.01); *A61M 2205/581* (2013.01); *A61M 2205/582* (2013.01)

(58) Field of Classification Search
CPC .. A61M 2005/2474; A61M 2039/1027; A61M 2205/581; A61M 2205/582; A61M 5/1413; A61M 5/142; A61M 5/14244; A61M 5/14546; A61M 5/14566
USPC ......................................................... 604/232
See application file for complete search history.

(56) References Cited

U.S. PATENT DOCUMENTS

| | | |
|---|---|---|
| 6,585,695 B1 | 7/2003 | Adair et al. |
| 6,659,980 B2 | 12/2003 | Moberg et al. |
| 6,854,620 B2 | 2/2005 | Ramey |
| 7,025,226 B2 | 4/2006 | Ramey |
| 7,033,338 B2 | 4/2006 | Vilks et al. |
| 7,628,782 B2 | 12/2009 | Adair et al. |
| 7,658,734 B2 | 2/2010 | Adair et al. |
| 7,981,105 B2 | 7/2011 | Adair et al. |
| 7,988,683 B2 | 8/2011 | Adair et al. |
| 7,998,131 B2 | 8/2011 | Adair et al. |

(Continued)

FOREIGN PATENT DOCUMENTS

EP 2 204 203 A2 7/2010

*Primary Examiner* — Jason E Flick
(74) *Attorney, Agent, or Firm* — Maier & Maier, PLLC

(57) ABSTRACT

A connector retains a medicine reservoir in a housing. The connector snaps onto the reservoir, the connector and reservoir are inserted into an aperture in the housing, and the connector snaps into the aperture in the housing. The connector may have a tubing and needle fixed in it to insert into the reservoir. The connector does not require a particular orientation when snapped into the housing and some embodiments may rotate freely. When snapped into the housing, the connector provides an auditory cue. For removal of the connector and reservoir, the exposed portion of the connector is compressed from the side. The configuration of the connector solves several problems associated with threaded connectors or other similar connectors.

15 Claims, 23 Drawing Sheets

(56) References Cited

U.S. PATENT DOCUMENTS

| | | |
|---|---|---|
| 8,257,345 B2 | 9/2012 | Adair et al. |
| 8,273,061 B2 | 9/2012 | McConnell et al. |
| 8,303,572 B2 | 11/2012 | Adair et al. |
| 8,500,716 B2 | 8/2013 | Adair et al. |
| 8,562,582 B2 | 10/2013 | Tuckwell et al. |
| 9,173,996 B2 | 11/2015 | Gray et al. |
| 2002/0173748 A1 | 11/2002 | McConnell et al. |
| 2004/0003493 A1 | 1/2004 | Adair et al. |
| 2005/0020980 A1 | 1/2005 | Inoue et al. |
| 2009/0137979 A1 | 5/2009 | Adair et al. |
| 2011/0060312 A1 | 3/2011 | Scheurer |
| 2012/0029431 A1* | 2/2012 | Hwang ............ A61M 5/14248 604/151 |
| 2014/0052077 A1 | 2/2014 | Holtwick et al. |
| 2015/0005716 A1 | 1/2015 | Adair et al. |

\* cited by examiner

CONNECTOR FOR MEDICATION DELIVERY SYSTEM

CROSS REFERENCE TO RELATED APPLICATIONS

This application claims priority to U.S. Provisional Application 62/063,386 filed on Oct. 13, 2015. The entirety of U.S. Provisional Application 62/063,386 including both the figures and specification are incorporated herein by reference.

TECHNICAL FIELD

This application relates generally to connectors, and more particularly to connectors used in medication delivery systems, e.g., systems used to deliver insulin and or other drugs to a person having diabetes and other health conditions.

BACKGROUND

People suffering from diabetes can require the administration of insulin and or other drugs to manage their blood glucose level within a normal range to avoid health problems, which can include one or more of cardiovascular disease, kidney damage, nerve damage, and blindness. It is important for the proper amount of insulin to be administered in a manner that is the same as the manner that insulin is produced by a person's pancreas, since both high and low glucose levels can result in adverse health complications for diabetics over an extended period of time.

Known systems used to deliver insulin to a person include those that provide basal insulin throughout the day, and selectively provide a bolus, or rapid-acting, dose of insulin during times when the user is consuming carbohydrates. Some conventional systems of this type include an insulin pump, and a reservoir or cartridge that contains insulin and is releasably attached to a pump housing. In some known systems, the reservoir is directly and releasably attached to a pump housing via mating threads of the reservoir and pump housing.

In other conventional systems, the reservoir is indirectly and releasably attached to the pump housing with a connector that is threadedly coupled with the reservoir and the pump housing.

In yet other known systems, threaded male and female leur fittings can be used in combination with respective adapters to couple a reservoir with a pump housing.

Each of these conventional systems further includes infusion tubing and or catheter or catheters that is in fluid communication with a chamber defined by the respective reservoir, to facilitate dispensing insulin contained within the chamber to the person.

BRIEF DESCRIPTION OF THE DRAWINGS

Various embodiments of a connector, for use in a medication delivery system, will become better understood with regard to the following description, appended claims, and accompanying drawings, wherein:

DETAILED DESCRIPTION

Figure 1:
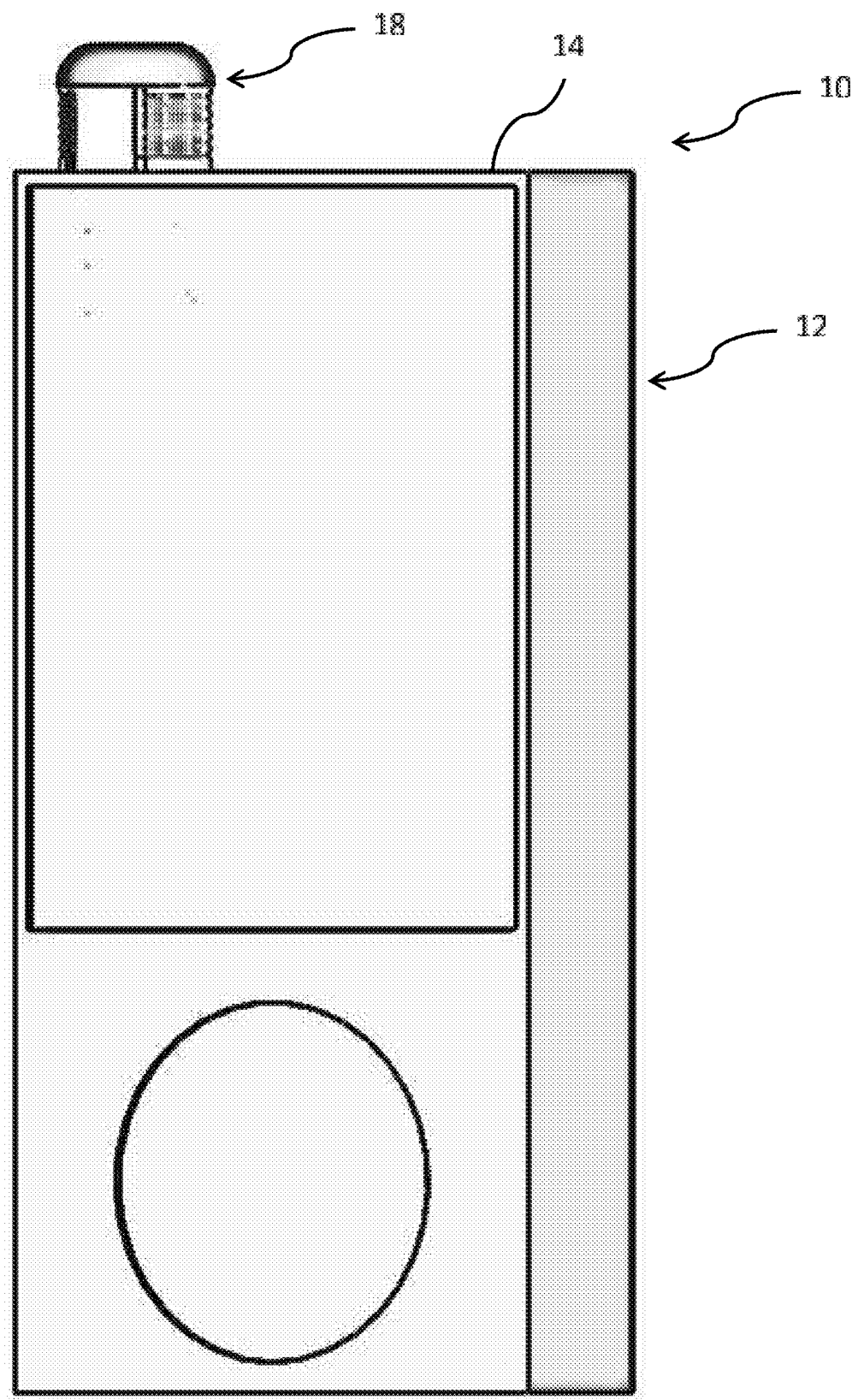
FIG. 1 is a perspective view of a portion of a medication delivery system according to one embodiment, depicting a portion of a pump, and a connector according to one embodiment, with the connector coupled with a pump housing of the pump.
Figure 2:
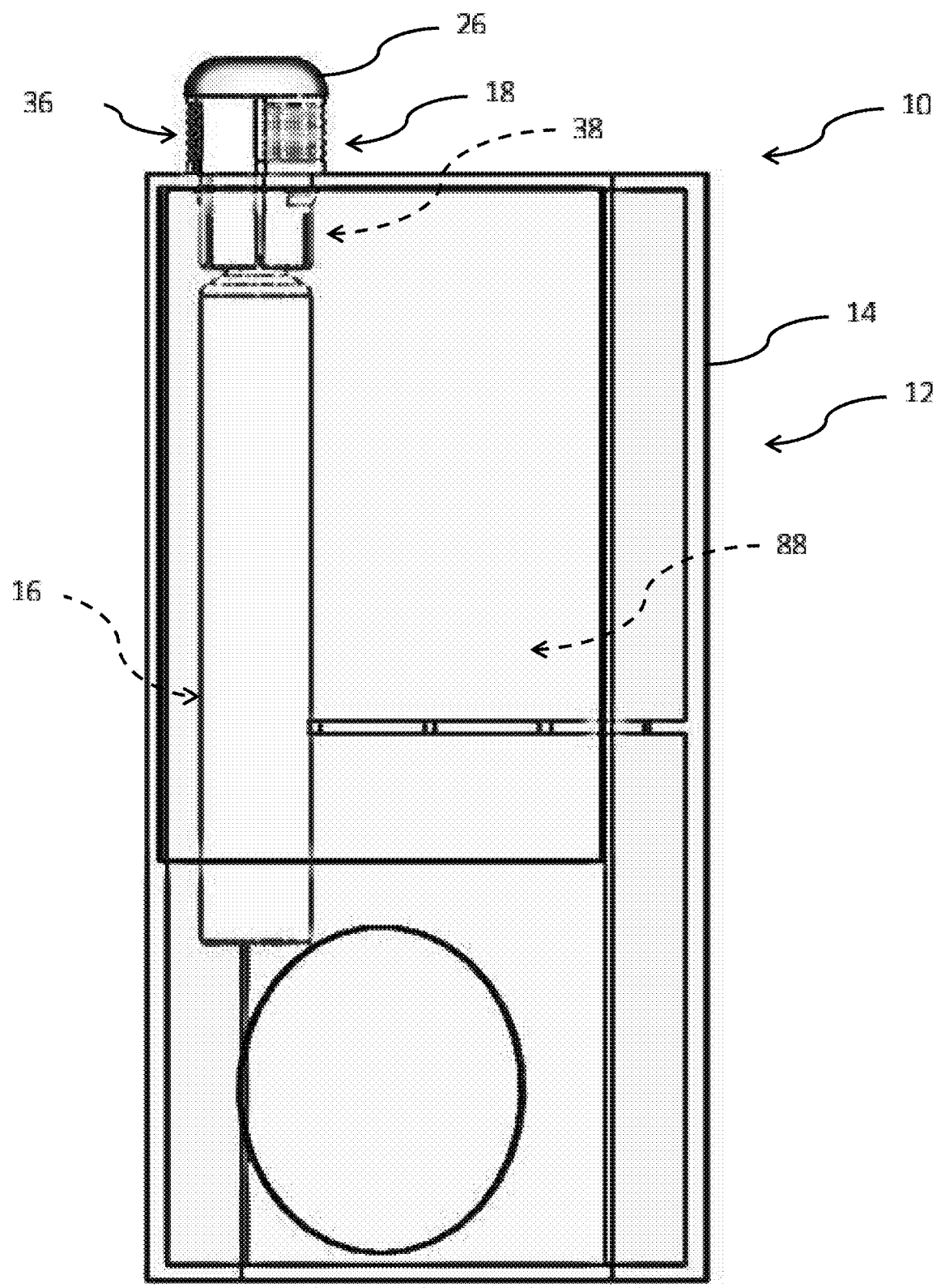
FIG. 2 is a perspective view similar to FIG. 1, but with a distal portion of the connector, and a reservoir coupled with the connector, positioned within a chamber defined by the pump housing.
Figure 2A:
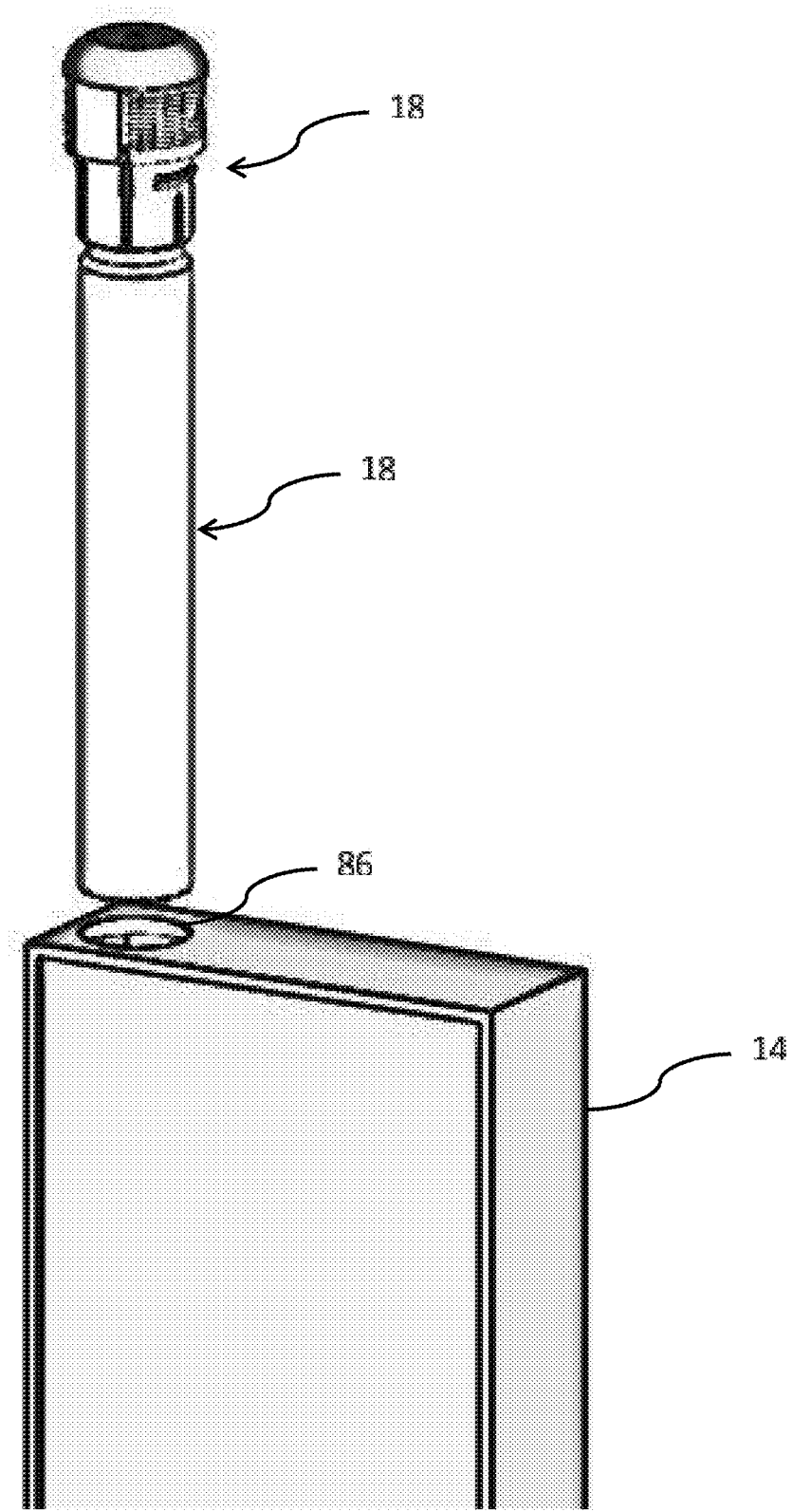
FIG. 2A is an exploded perspective view depicting a portion of the pump of FIGS. 1 and 2, with the connector and the reservoir spaced from the pump.
Figure 2B:
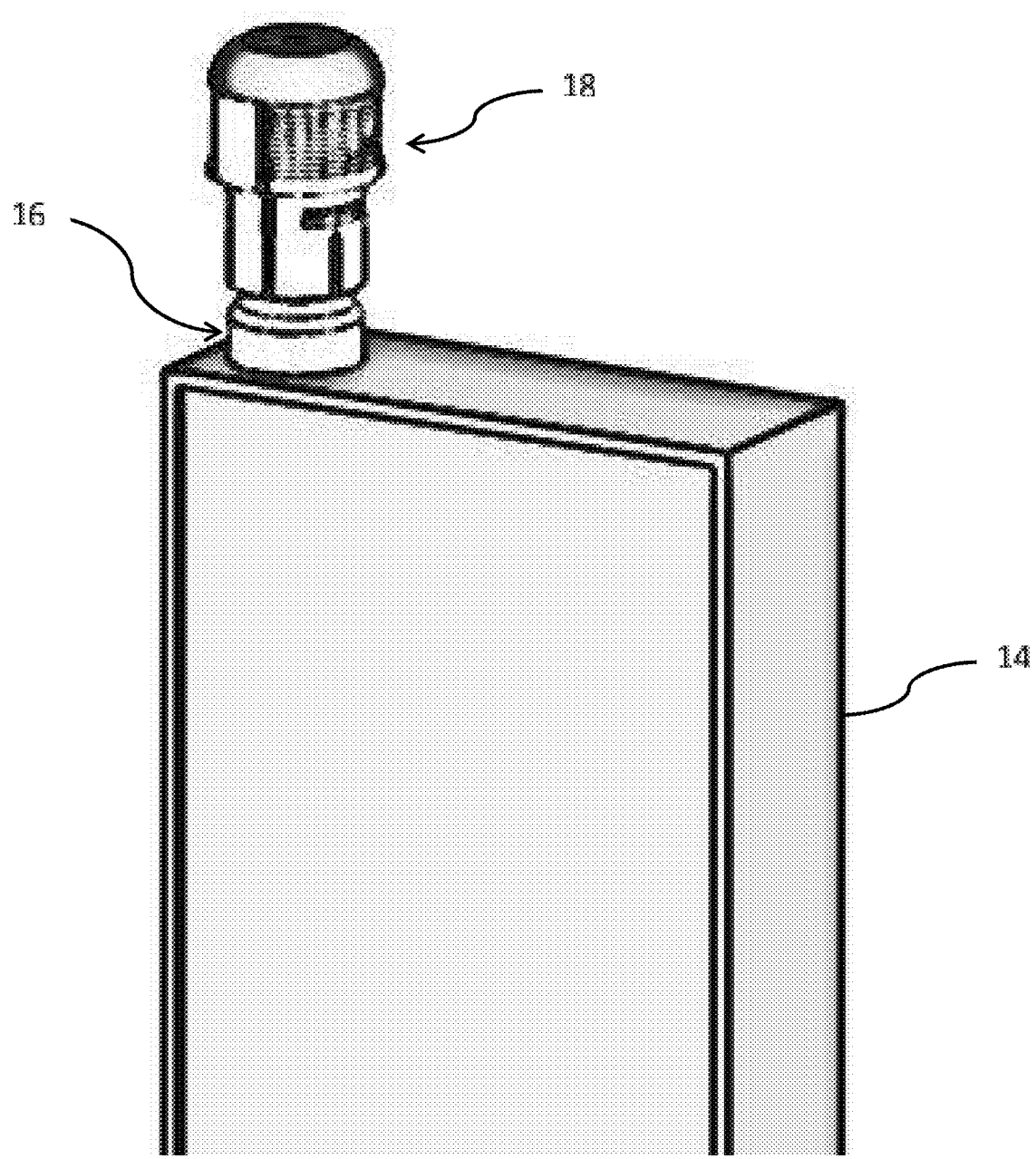
FIG. 2B is a perspective view depicting a portion of the pump of FIGS. 1 and 2, with a portion of the reservoir, and the connector, protruding above the pump.
Figure 3:
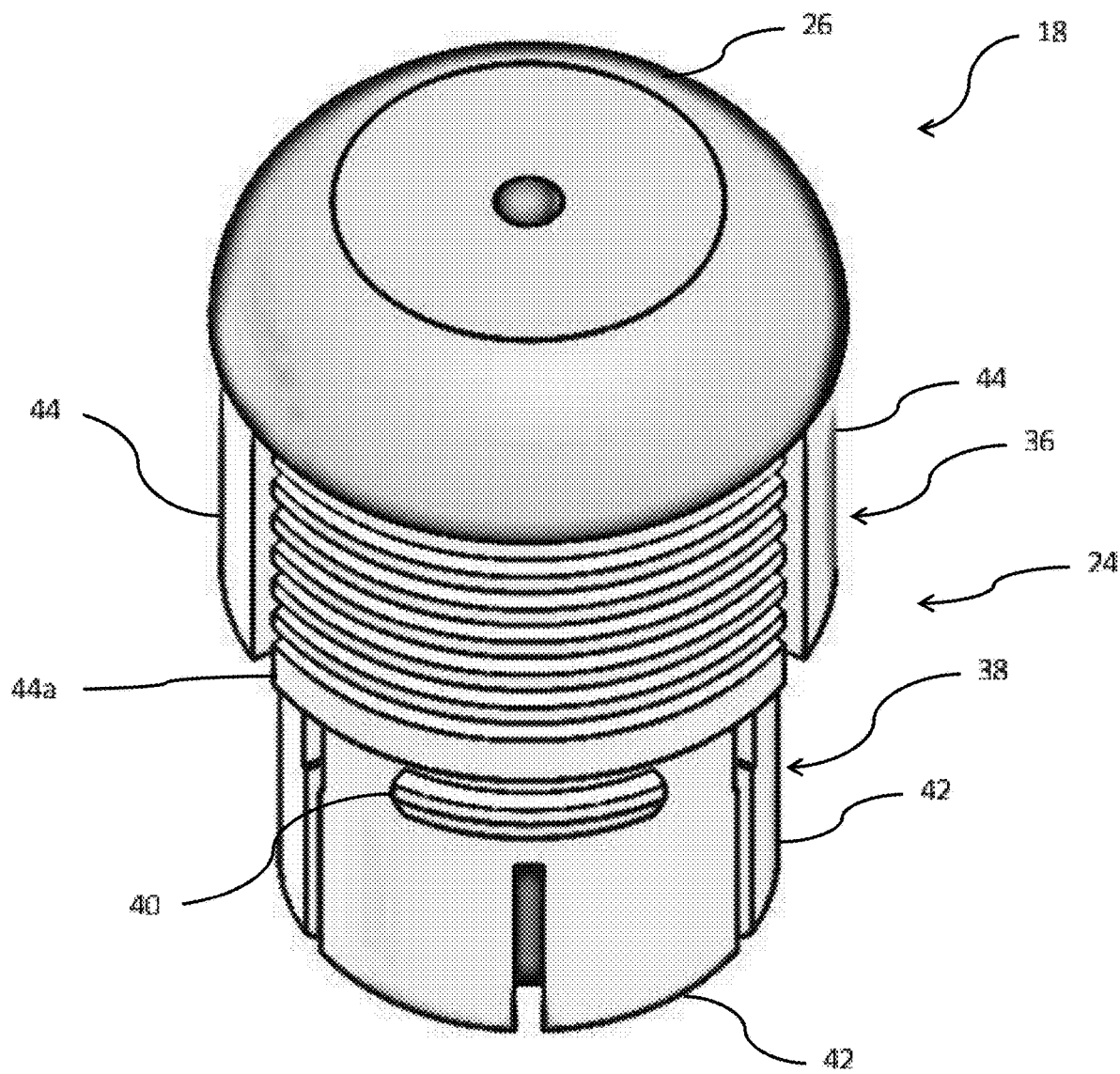
FIG. 3 is a perspective view of the connector of the system depicted partially in FIGS. 1 and 2.
Figure 4:
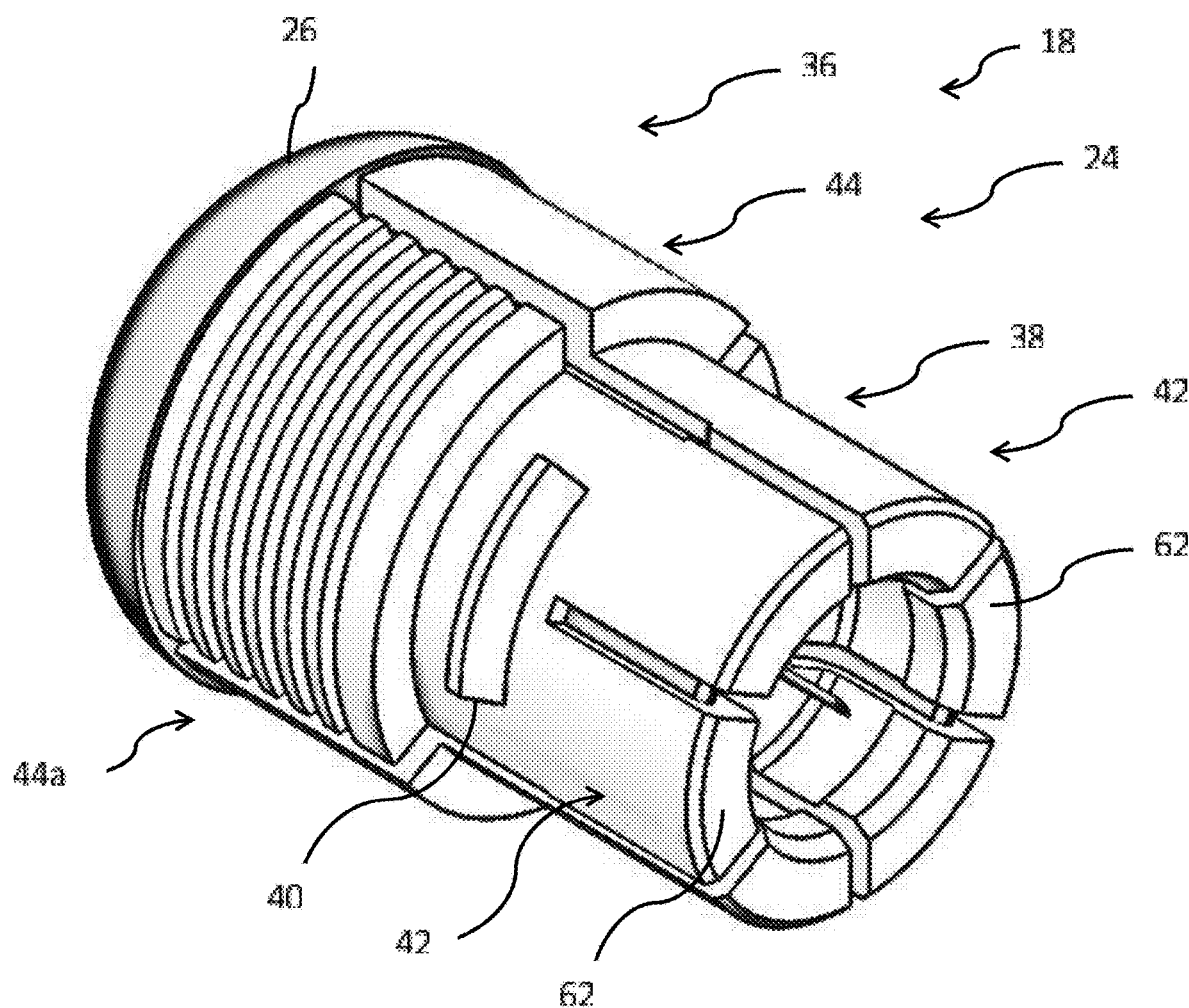
FIG. 4 is a perspective view of the connector of FIG. 3.
Figure 5:
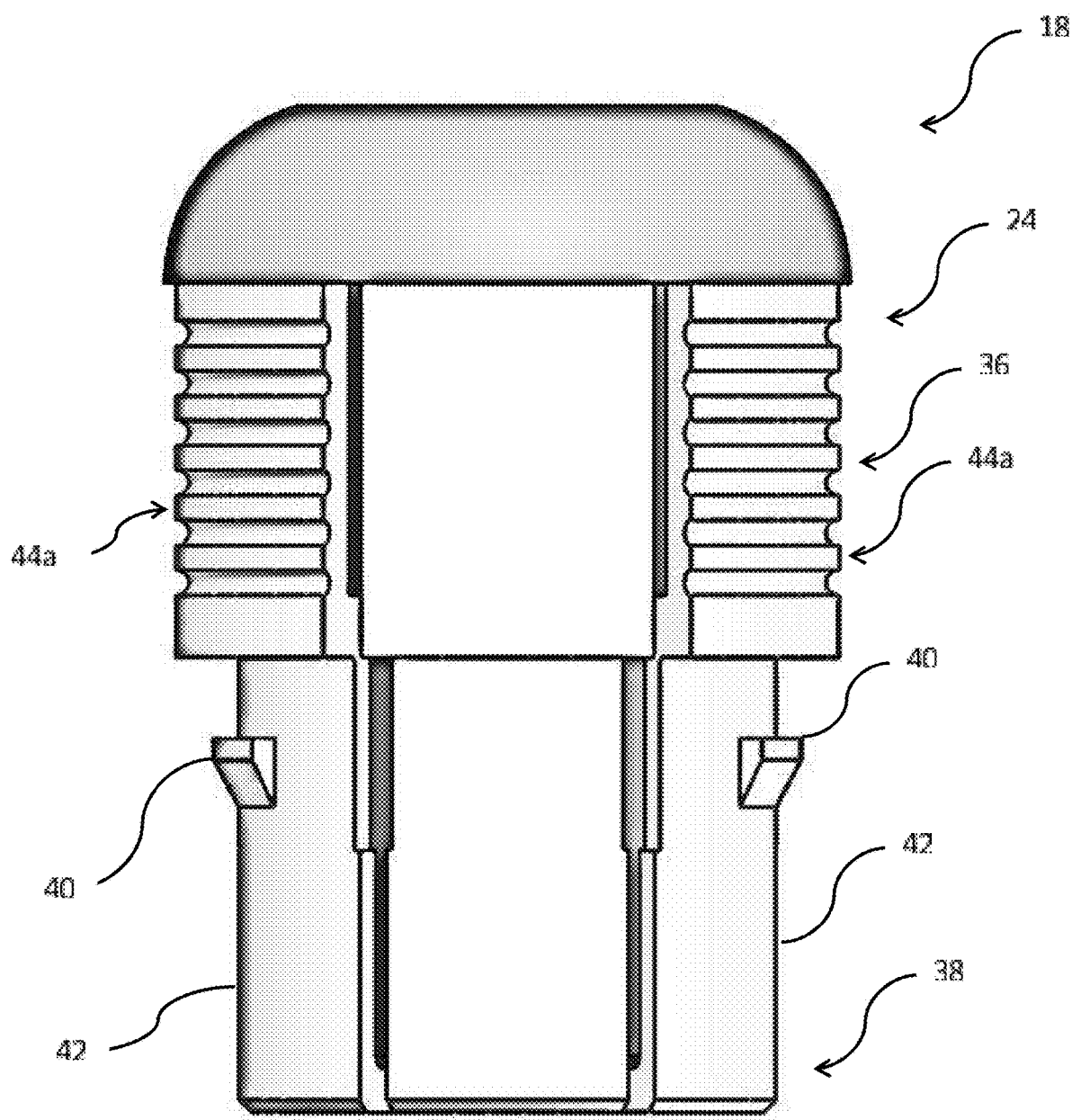
FIG. 5 is an elevational view of the connector of FIG. 3.

Referring to the drawings, wherein like reference numbers indicate the same or corresponding elements throughout the drawings, FIGS. 1-2 illustrate a portion of a medication delivery system, indicated generally at 10. System 10 can include an infusion pump 12 (FIGS. 1 and 2) which can include a pump housing 14. System 10 can also include a reservoir 16, which can be configured to retain a medication (e.g., insulin, or any one of a variety of other medications) and a connector 18. The connector 18 can be attached to the reservoir 16 and can be releasably attached to the pump housing 14. The medication delivery system 10 can also include infusion tubing 20 and a needle 22 to facilitate delivery of a medication contained within the reservoir 16 to a person (not shown), e.g., as subsequently described.

Referring to FIGS. 3-8, the connector 18 can include a body 24 and a plug 26. Body 24 can be made, e.g., by forming or machining, from a polymeric material, e.g., any one of a variety of thermoplastic materials. The plug 26 can be made separately from body 24, and secured to body 24, e.g., by a friction fit, as shown in FIGS. 3-8. The plug 26 can be made from an elastomeric material, e.g., natural or synthetic rubber. Alternatively, plug 26 can be formed or machined from a polymeric material, e.g., any one of a variety of thermoplastic materials. As another alternative, connector 18 can be made as a unitary construction, e.g., by integrally forming body 24 and plug 26 from a thermoplastic material as a unitary construction.

Body 24 of connector 18 can include a proximal portion 36 and a distal portion 38 integral with the proximal portion 36. Connector 18 can also include at least one retention member 40. In the illustrative embodiment, connector 18 is shown to include two of the retention members 40. In other embodiments, connectors can be provided with one, or more than two, retention members 40. Each of the retention members 40 can be movable between a first, outward position, shown in FIGS. 3-8, and a second, inward position (not shown). In embodiments including more than one retention member 40, e.g., as shown in FIGS. 3-8, the retention members 40 can be circumferentially spaced.

The distal portion 38 of body 24 of connector 18 can include a plurality of flexible fingers 42, which can be circumferentially spaced from one another. Each of the retention members 40 can extend outwardly from a respective one of the flexible fingers 42. The proximal portion 36 of body 24 of connector 18 can include a plurality of circumferentially spaced sections 44. Each of the sections 44 can be aligned with, and integral with a respective one of the flexible fingers 42. One or more of the sections 44 of the proximal portion 36 can be a ribbed section. In the embodiment of FIGS. 3-8, the proximal portion 36 is shown to include two ribbed sections, which are each designated 44a. Each of the ribbed sections 44a is aligned with a respective one of the flexible fingers 42 and is aligned with a respective one of the retention members 40. Inward compression of any one of the circumferentially spaced sections 44 of the proximal portion 36 of body 24 can cause an inward movement of the aligned one of the flexible fingers 42 of the distal portion 38 of body 24. For example, inward compression of the ribbed sections 44a of proximal portion 36, for example, by a user's hand, can cause an inward movement of the aligned ones of the flexible fingers 42 and an inward movement of the aligned ones of the retention members. Each ribbed section 44a can include a plurality of ribs that facilitate grasping sections 44a.

The reservoir 16 can include a neck 50 and a body 52, which can cooperate to define a reservoir chamber that can be configured to retain a medication, e.g., insulin. The reservoir 16 can include a septum 53 attached to the neck 50, which can close the chamber, in combination with a plunger (not shown) positioned within the chamber. Other embodiments of reservoir 16 may not have a septum 53, but rather a connector such as a luer connector or fitting. This connector may thread onto reservoir 16. The distal portion 38 of body 24 can define a recessed portion 60 (FIG. 6), which can be configured to receive at least a portion of the neck 50 of reservoir 16. Each of the flexible fingers 42 can be configured to engage the neck 50, to attach the connector 18 to the reservoir 16. For example, in one embodiment, each of the flexible fingers 42 can include a lip 62 that can engage the neck 50.

Figure 6:
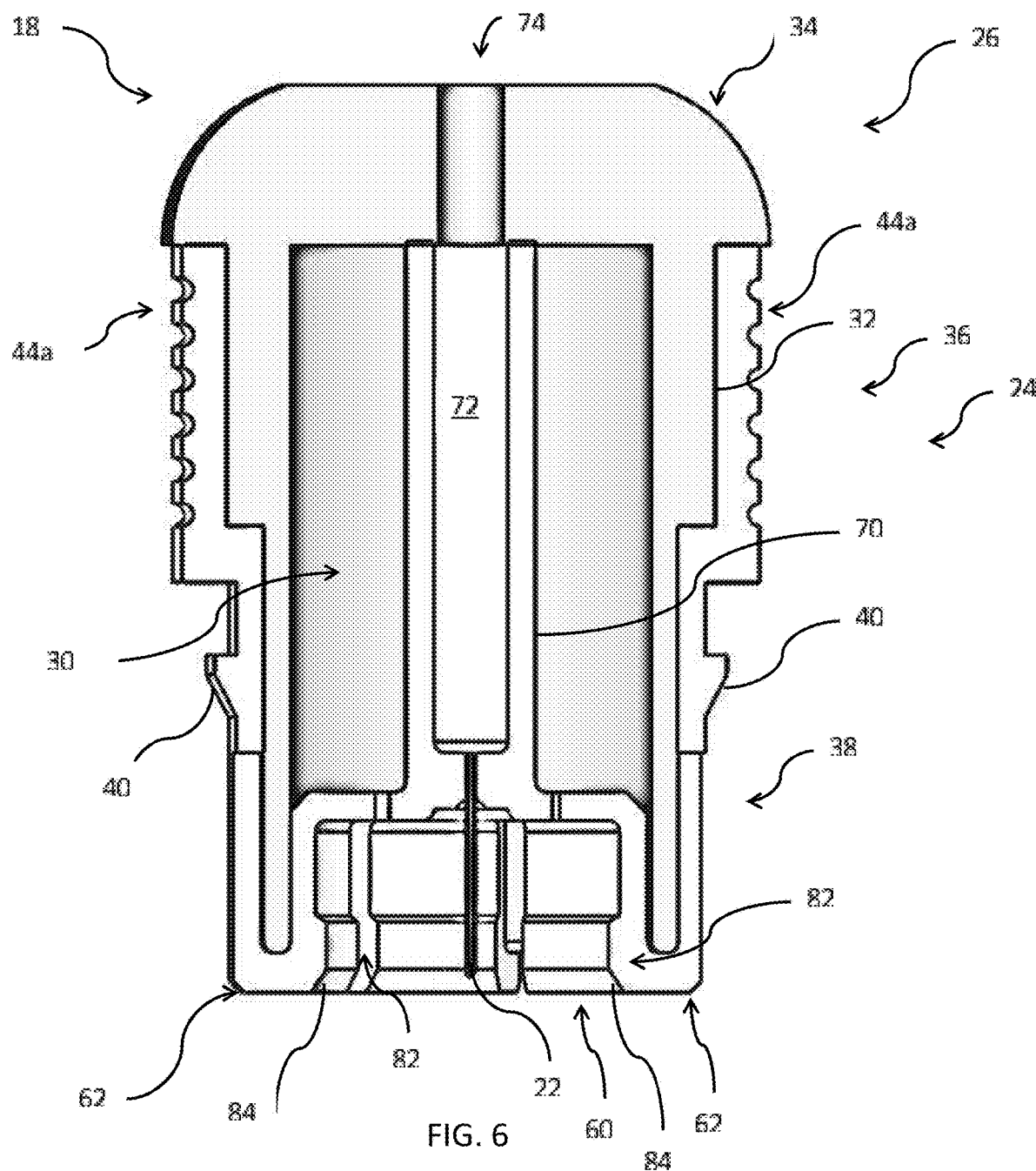
FIG. 6 is a longitudinal cross-sectional view of the connector of FIG. 3.
Figure 7:
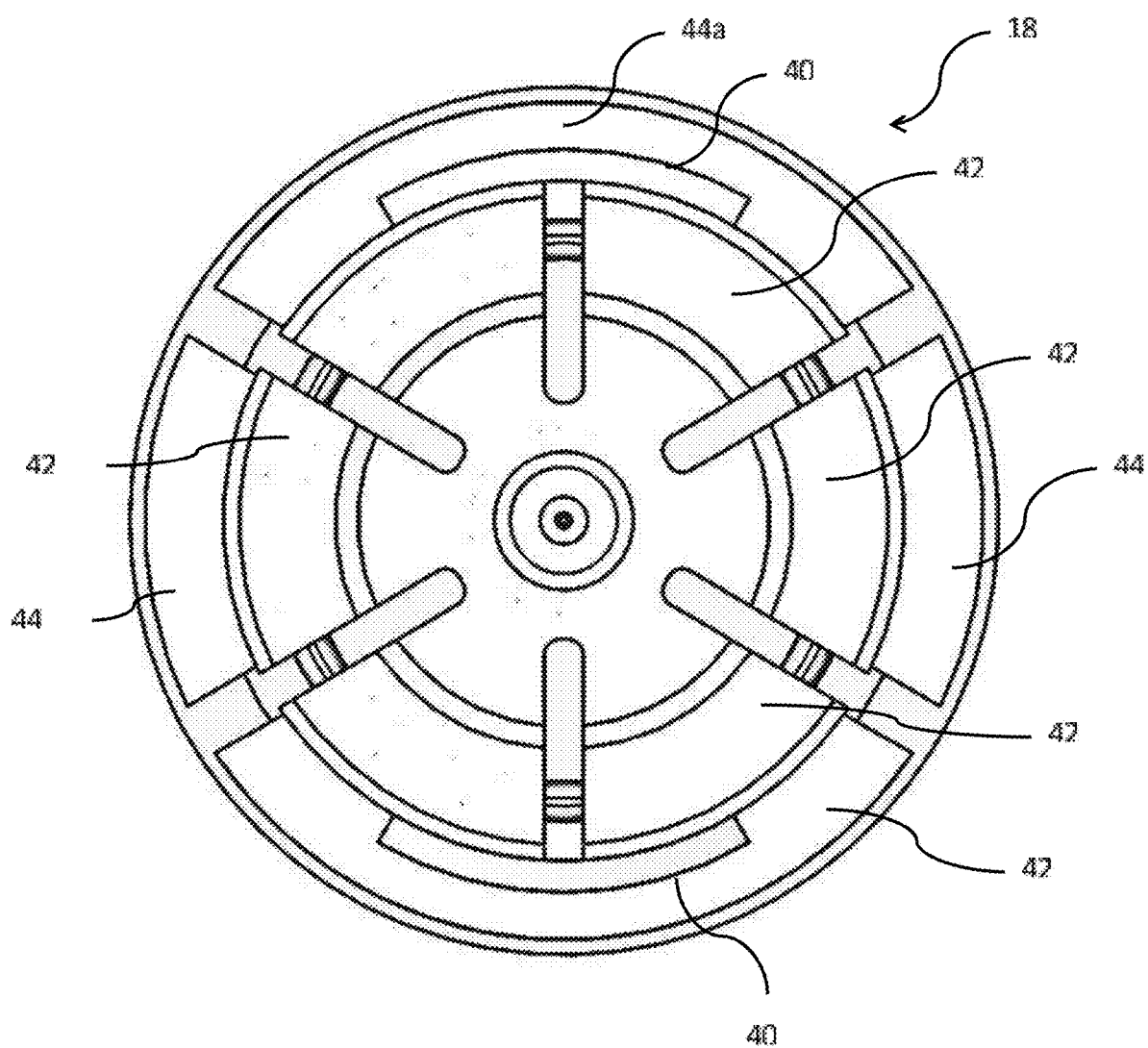
FIG. 7 is an end view of the connector of FIG. 3.
Figure 8:
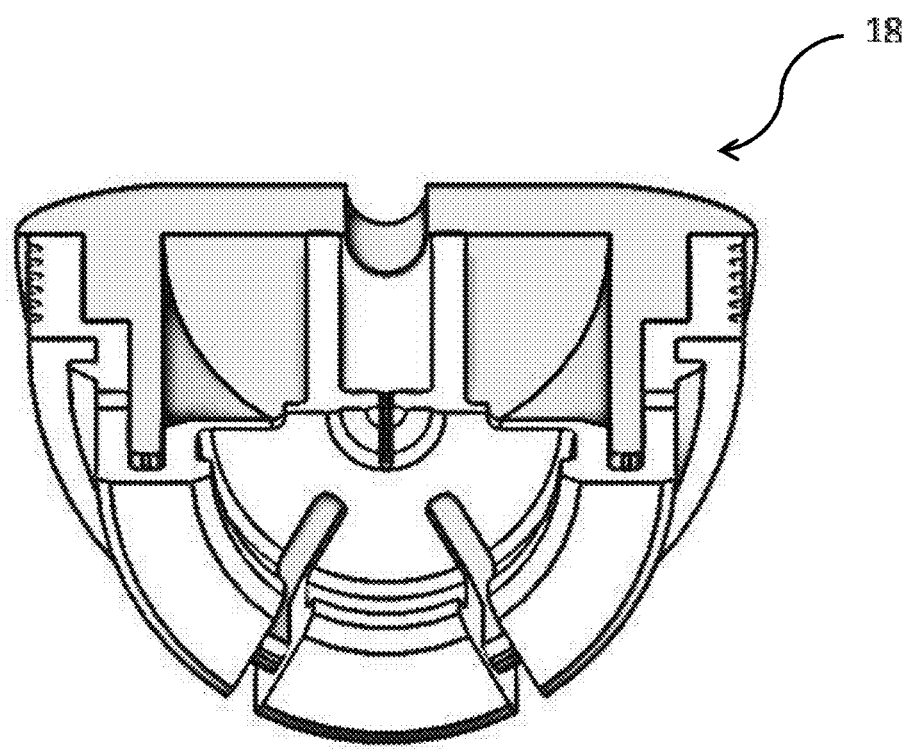
FIG. 8 is a perspective view depicting a portion of the connector of FIG. 3.
Figure 9:
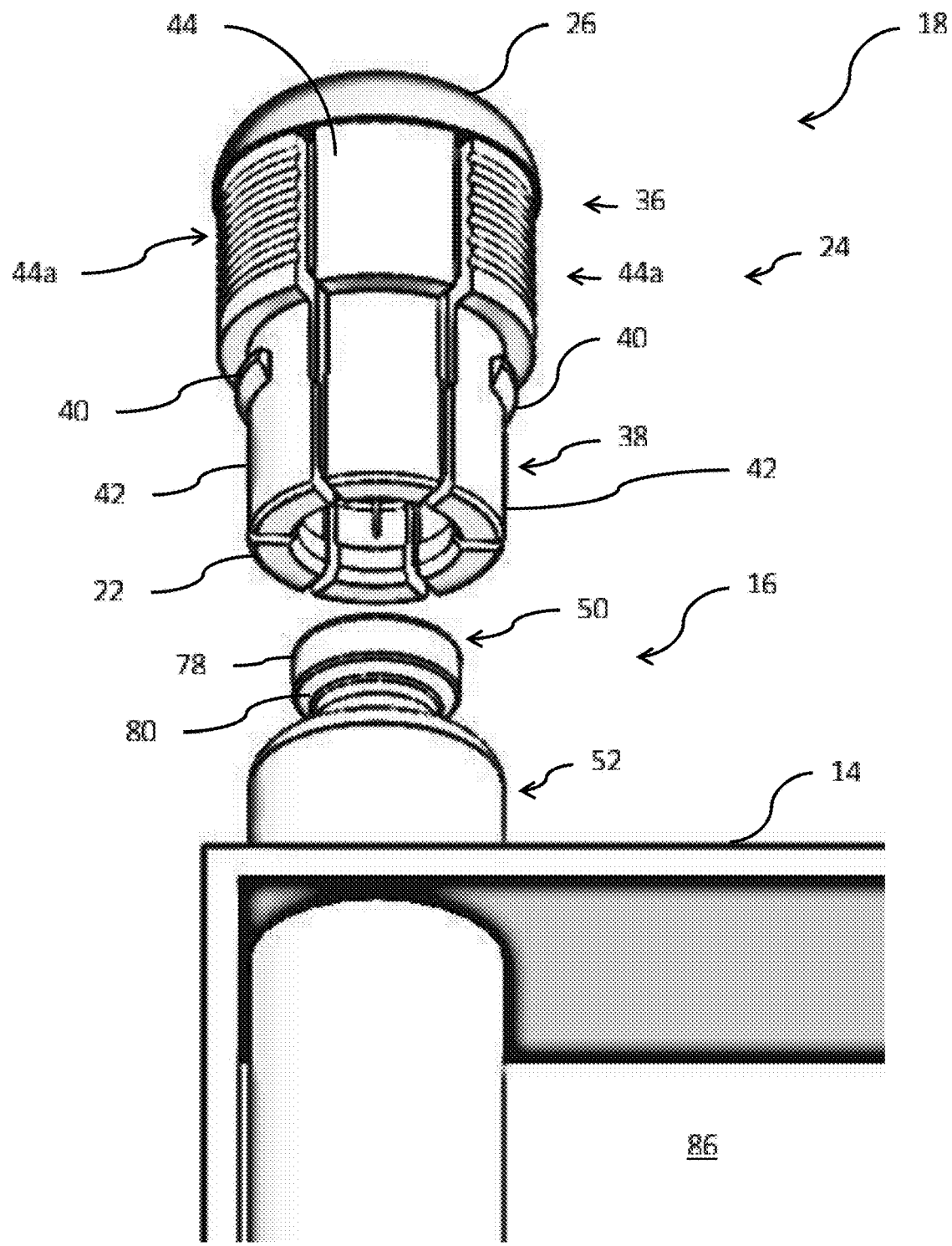
FIG. 9 is an exploded perspective view.
Figure 10:
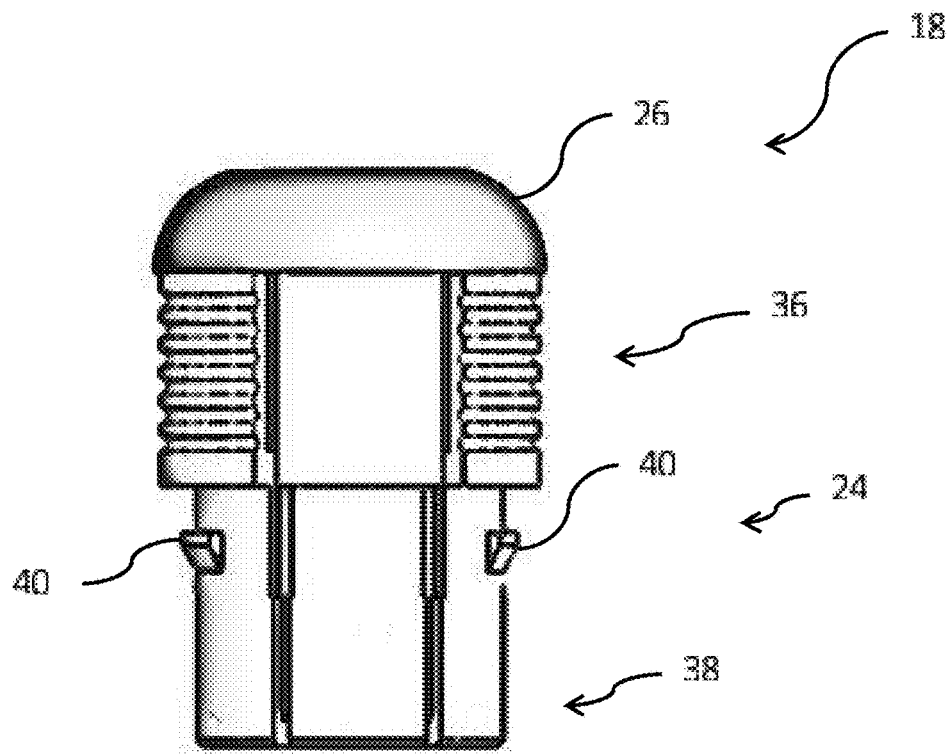
FIG. 10 is an exploded elevational view, of the medication delivery system shown partially in FIGS. 1 and 2, depicting the connector spaced from the reservoir and depicting the reservoir extending through an aperture defined by the pump housing.
Figure 10:
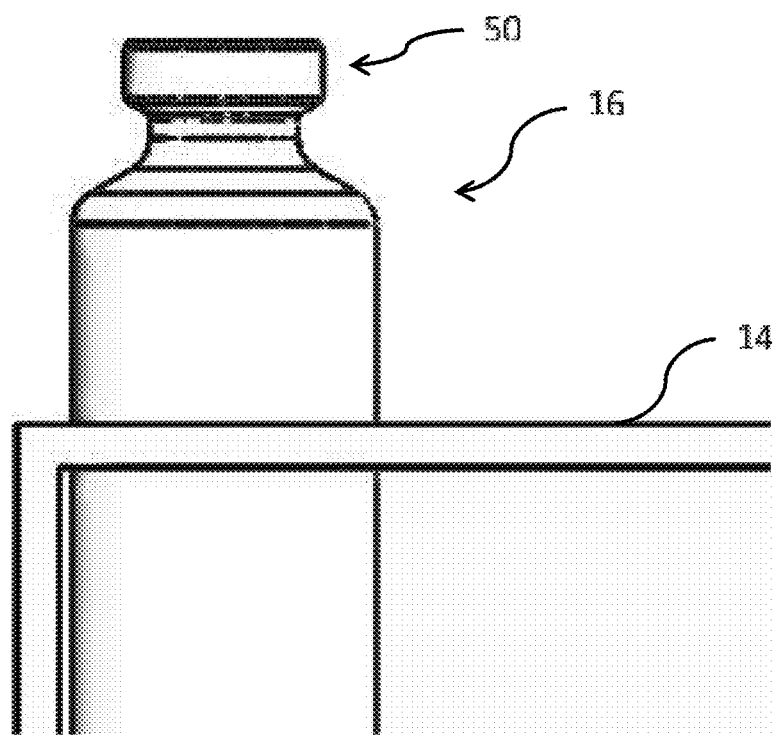
Figure 11:
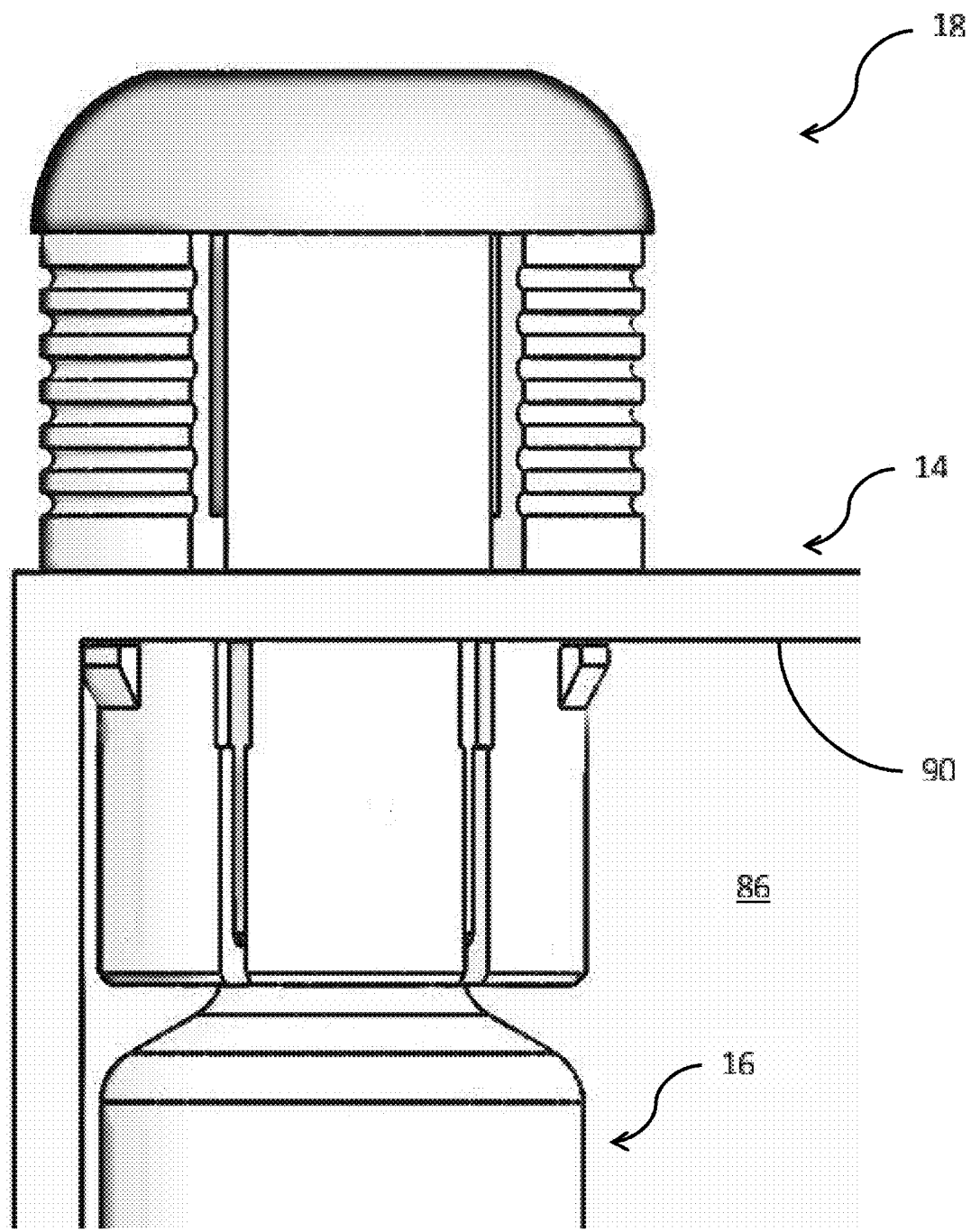
FIG. 11 is an elevational view, similar to the exploded view of FIG. 10, but with the connector coupled with the reservoir, which is disposed within the pump housing, and with the connector coupled with the pump housing, with retention members of the connector engaged with an interior surface of the pump housing.
Figure 12:
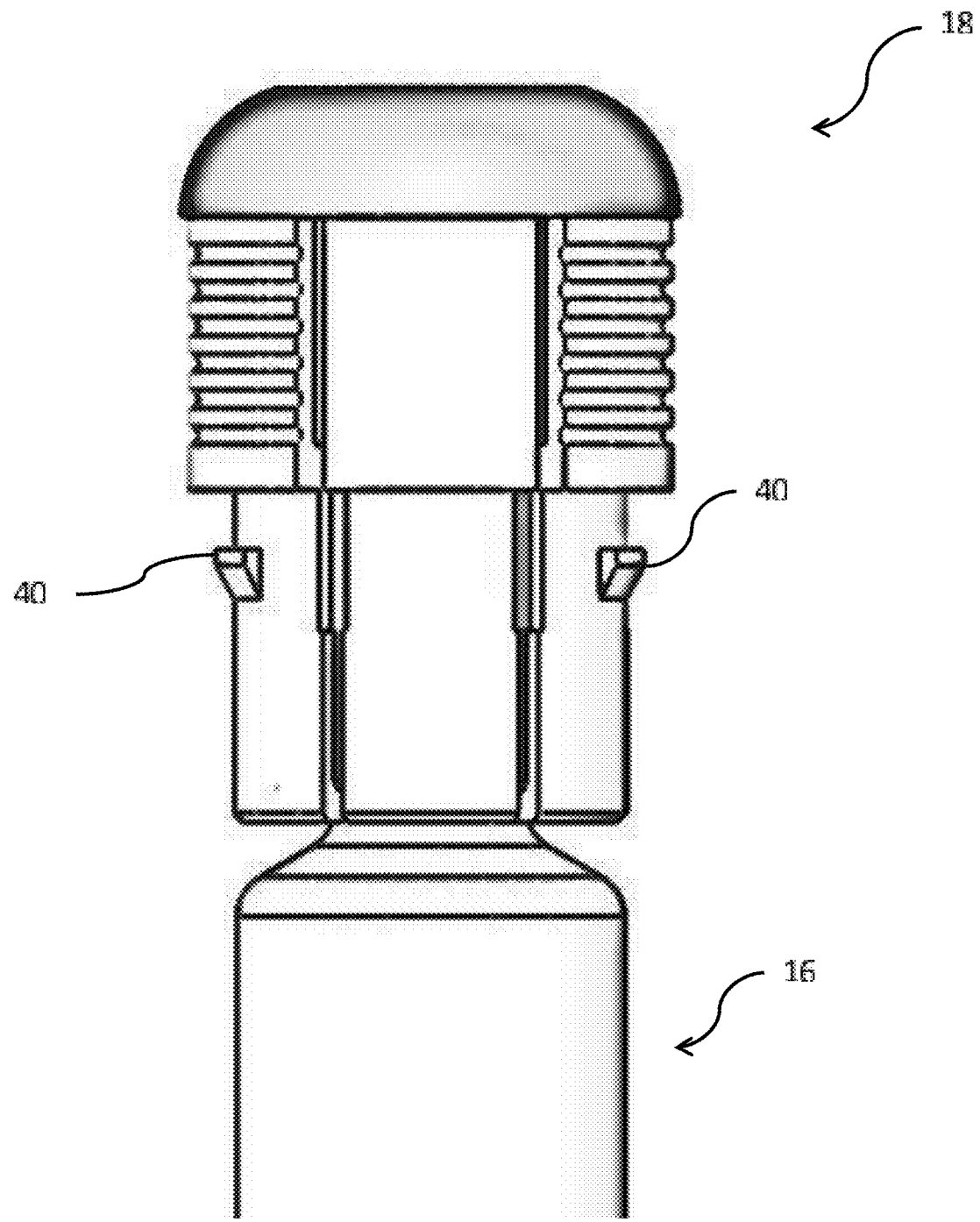
FIG. 12 is an elevational view similar to FIG. 11, but with the pump housing omitted.
Figure 13:
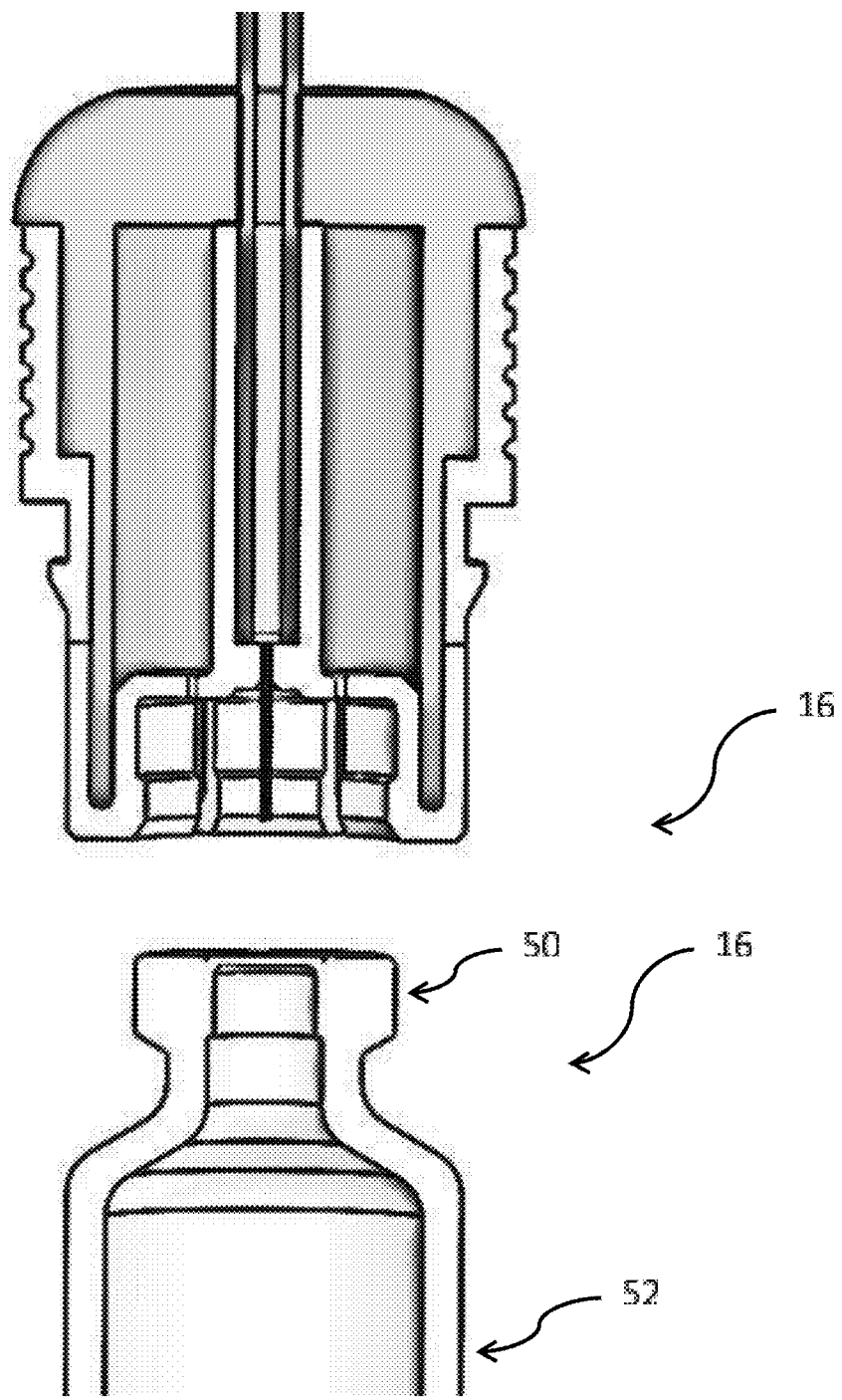
FIG. 13 is an exploded cross-sectional view, depicting the connector and a portion of the reservoir of the medication delivery system.
Figure 14:
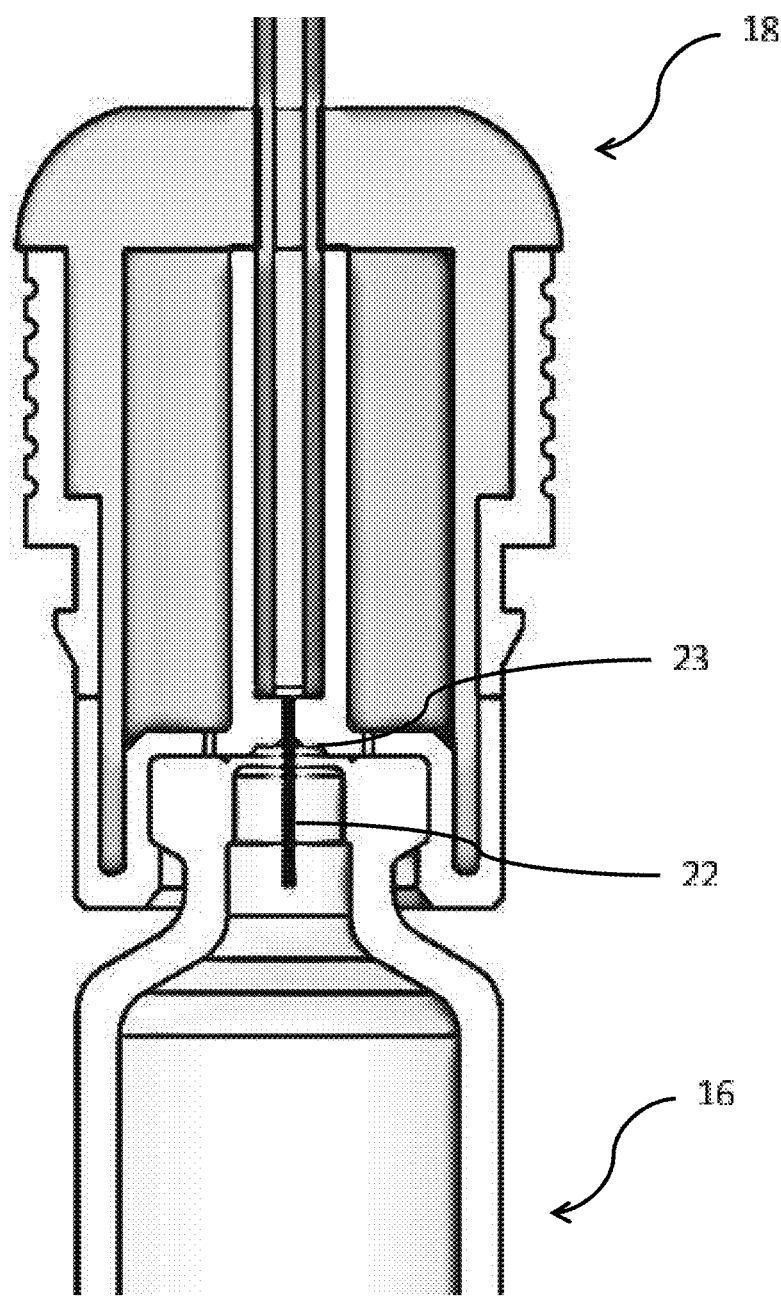
FIGS. 14 and 15 are cross-sectional views depicting a portion of the connector and a portion of the reservoir of the medication delivery system with the connector attached to the reservoir.
Figure 15:
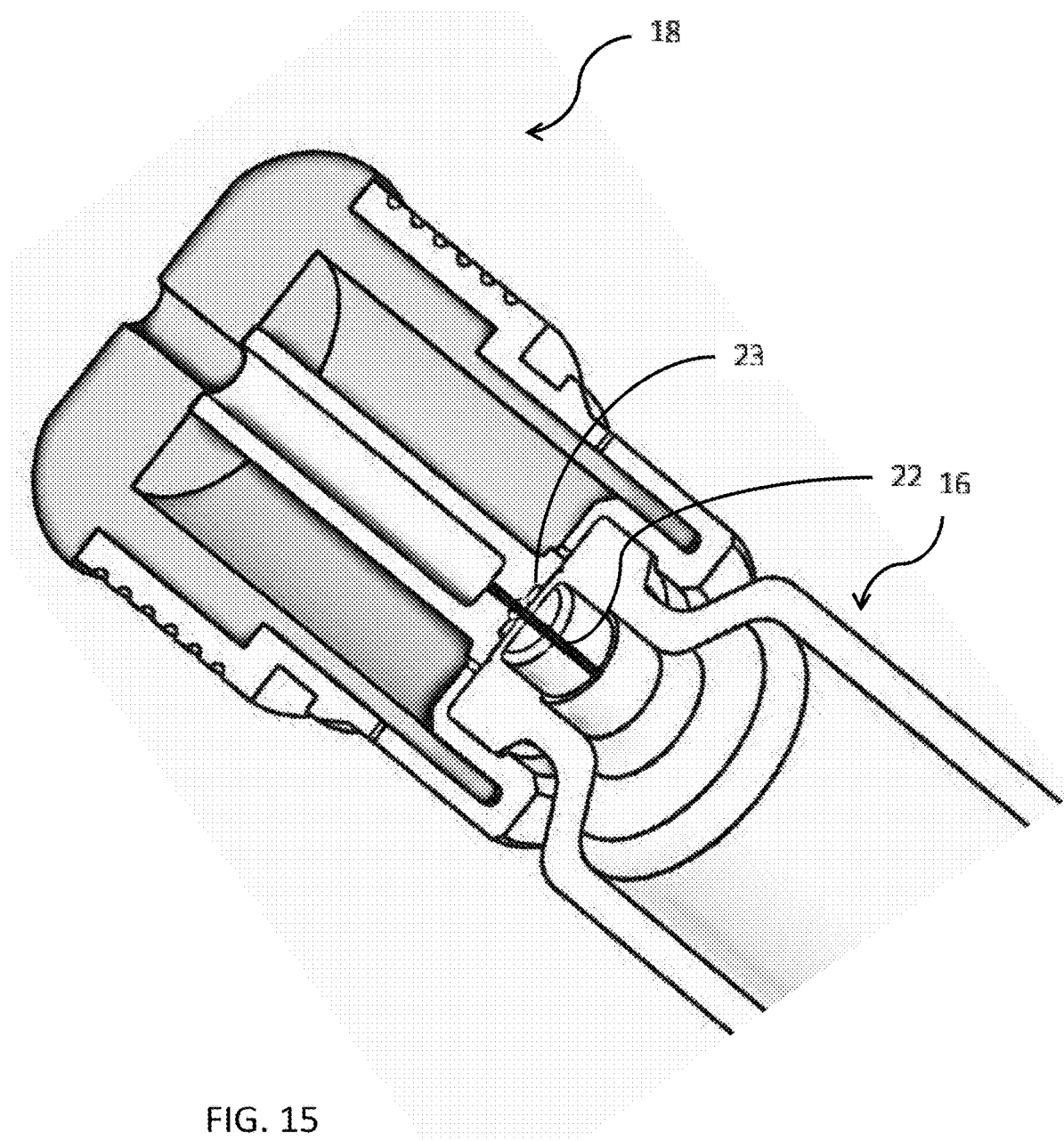

As shown in FIGS. 6 and 13, the needle 22 can be positioned within the interior chamber 30 defined by the body 24 of connector 18. In one embodiment, the needle 22 can be integrally formed with at least the body 24 of connector 18 (e.g., using insert molding). In other embodiments, the needle 22 can be made separately from connector 18 and can be secured to connector 18 in any suitable manner, e.g., by bonding the needle 22 to connector 18.

As shown in FIG. 13, the body 24 of connector 18 can include a stem 70 extending longitudinally within the interior chamber 30. Stem 70 can define a passage 72 from its distal end to its proximal end, which can be sized and configured to receive a distal portion of tubing 20. The tubing can be swaged, or otherwise secured, to needle 22 to facilitate fluid communication between a hollow interior of needle 22 and a hollow interior of tubing 20. The plug 26 of connector 18 can define a passage 74, which can be aligned with passage 72, and which can communicate with passage 72 so that tubing 20 can be inserted into and through passage 74 and passage 72. Each of the flexible fingers 42 can be attached to the distal end of the stem 70. The distal end of the stem 70 can be intermediate of a distal end and proximal end of each of the flexible fingers 42.

Referring to FIGS. 1-2, 14, and 9-15, in one embodiment, connector 18 can be attached to reservoir 16 by inserting the neck 50 of reservoir 16 into the recessed portion 60 defined by the distal portion 38 of body 24 of connector 18. When the connector 18 is attached to the reservoir 16, the needle 22 can pierce the septum 53 to provide fluid communication between the chamber defined by the reservoir and the hollow interior of needle 22. During this process a relatively larger portion 78 of neck 50 can force the flexible fingers 42 of the distal portion 38 of body 24 outwardly. The distal portion 38 and a relatively smaller portion 80 of neck 50 can be configured such that the flexible fingers 42 can move inwardly. The inward movement of flexible fingers 42 can cause an inwardly extending portion 82 of the lip 62 of each of the flexible fingers 42 to engage the neck 50 of reservoir 16, which can attach connector 18 to reservoir 16. The lip 62 of each of the flexible finger 42 can include a lead-in chamfer 84, which can facilitate insertion of the neck 50 of reservoir 16 into the recessed portion 60 defined by the distal portion 38 of connector 18.

The subassembly of reservoir 16 and connector 18 can be releasably attached to the pump housing 14 of pump 12 in the following manner, in one embodiment. The reservoir 16 and the distal portion 38 of connector 18 can be inserted through an aperture 86 defined by the pump housing 14, into a chamber 88 defined by the pump housing 14. The user can compress the ribbed sections 44a of the proximal portion 36 of connector 18, which can cause the flexible fingers 42 and the retention members 40 to move inwardly to permit the distal portion 38 of connector 18 to pass through the aperture 86.

Once the retention members 40 pass through aperture 86, the flexible fingers 42 and the retention members 40 can move to their respective outward positions. The flexible fingers 42 and retention members 40 can move in a "snapping action" to their respective outward positions. The retention members 42 can make an audible clicking sound as they are snapped into their outward positions. When the retention members 40 are in their outward positions, the retention members 40 can engage the pump housing 14, which can prevent the connector 18 and reservoir 16 from moving in a proximal direction relative to the pump housing 14. In one embodiment, the retention members 40 can engage an inner surface 90 of pump housing 14. In other embodiments (not shown) the retention members 40 can engage the threads of a threaded aperture of a pump housing.

The releasable engagement of connector 18 with pump housing 14 can be achieved without any mating threads or cam surfaces, i.e., both the connectors 18 and reservoir 16 can be devoid of threads or cam surfaces as shown in FIGS.

13-15, such that the releasable attachment of connector 18 to pump housing 14 can be achieved without any rotation of the connector 18 or reservoir 16. The connector 18 and reservoir 16 can be disengaged with the pump housing 14 by compressing the ribbed portions 44a of the proximal portion 36 of connector 18, and pulling the connector 18 in a proximal direction.

Figure 16:
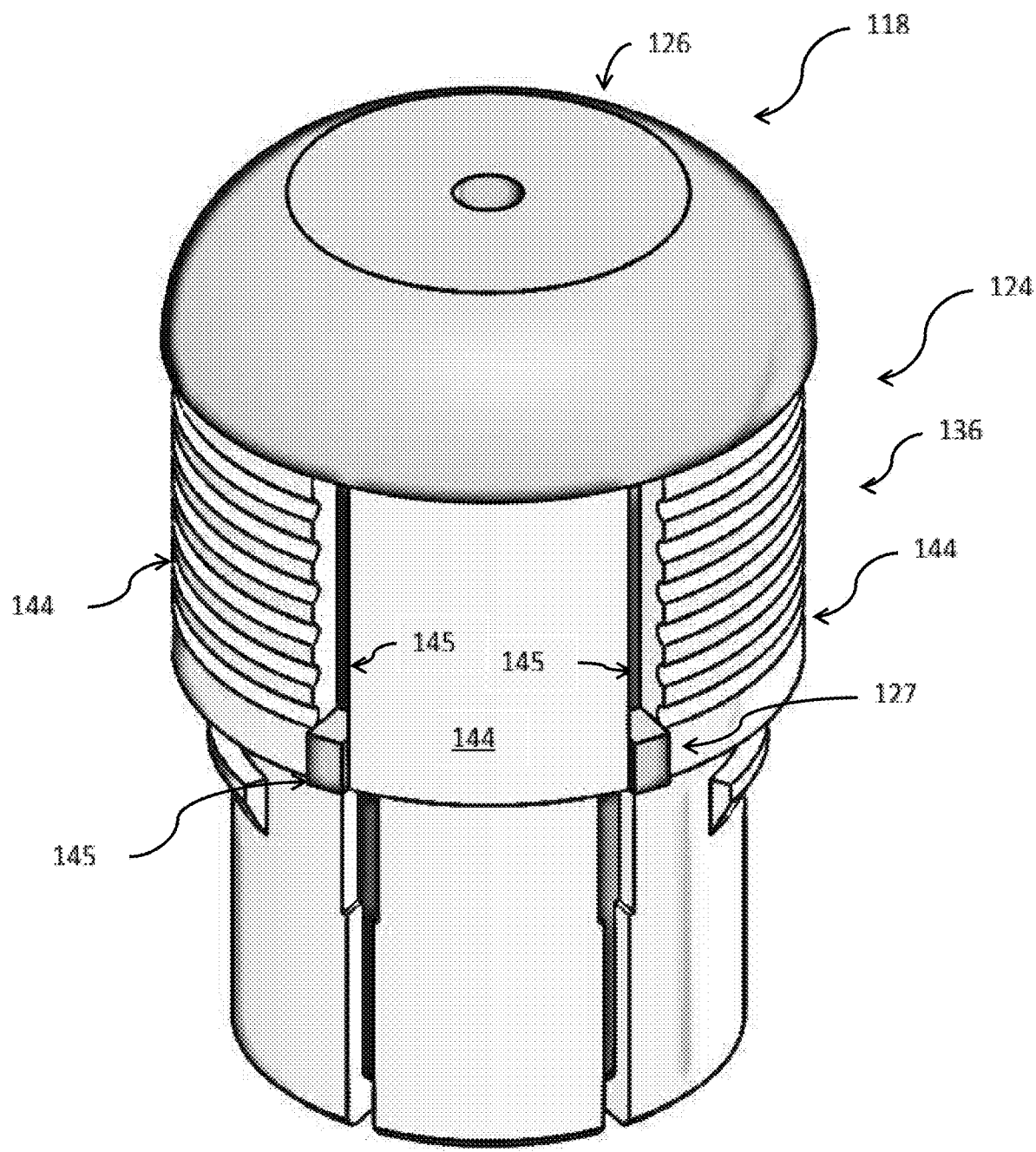
FIGS. 16-18 are perspective views depicting a connector of a medication delivery system, according to another embodiment.
Figure 17:
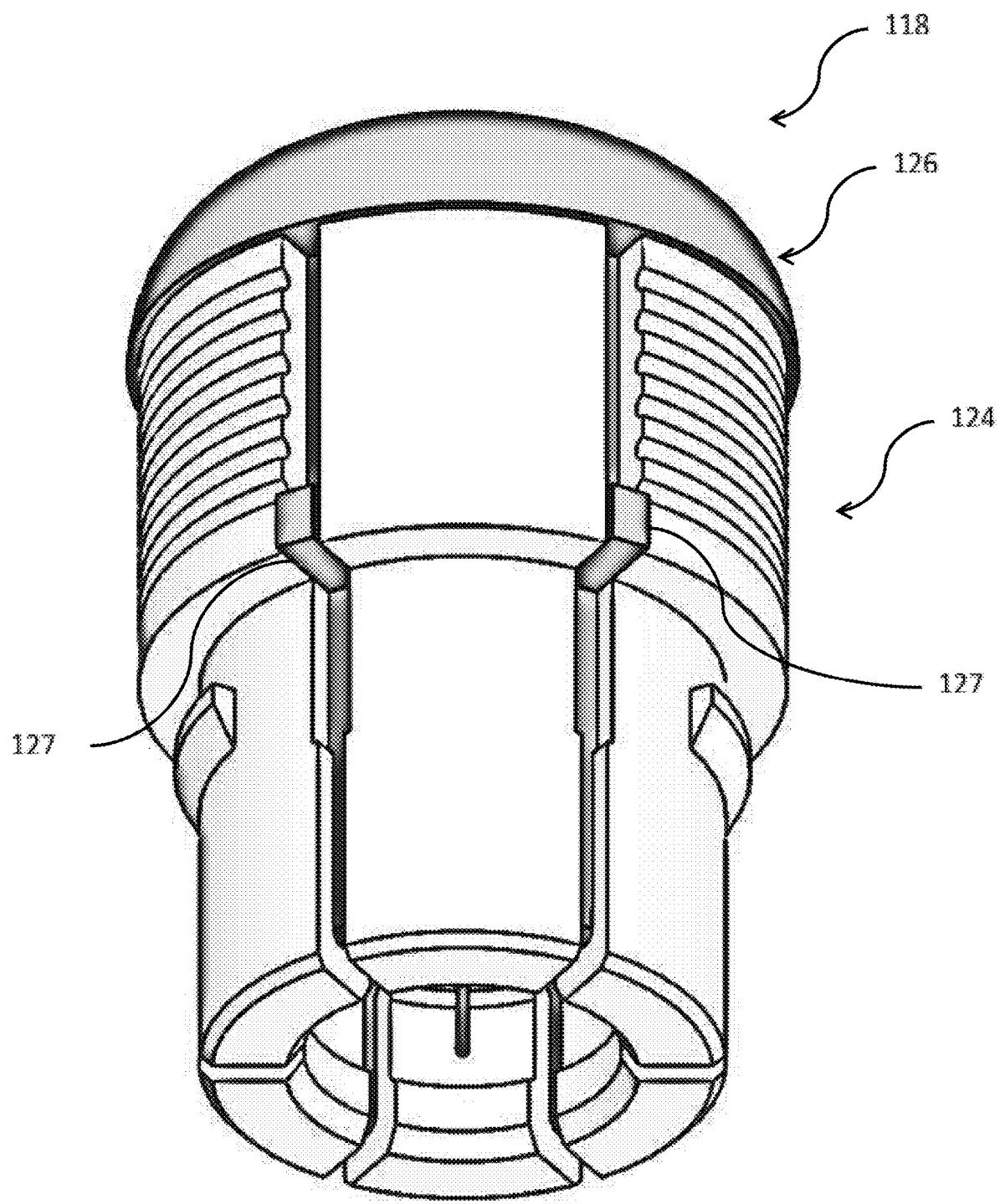
Figure 18:
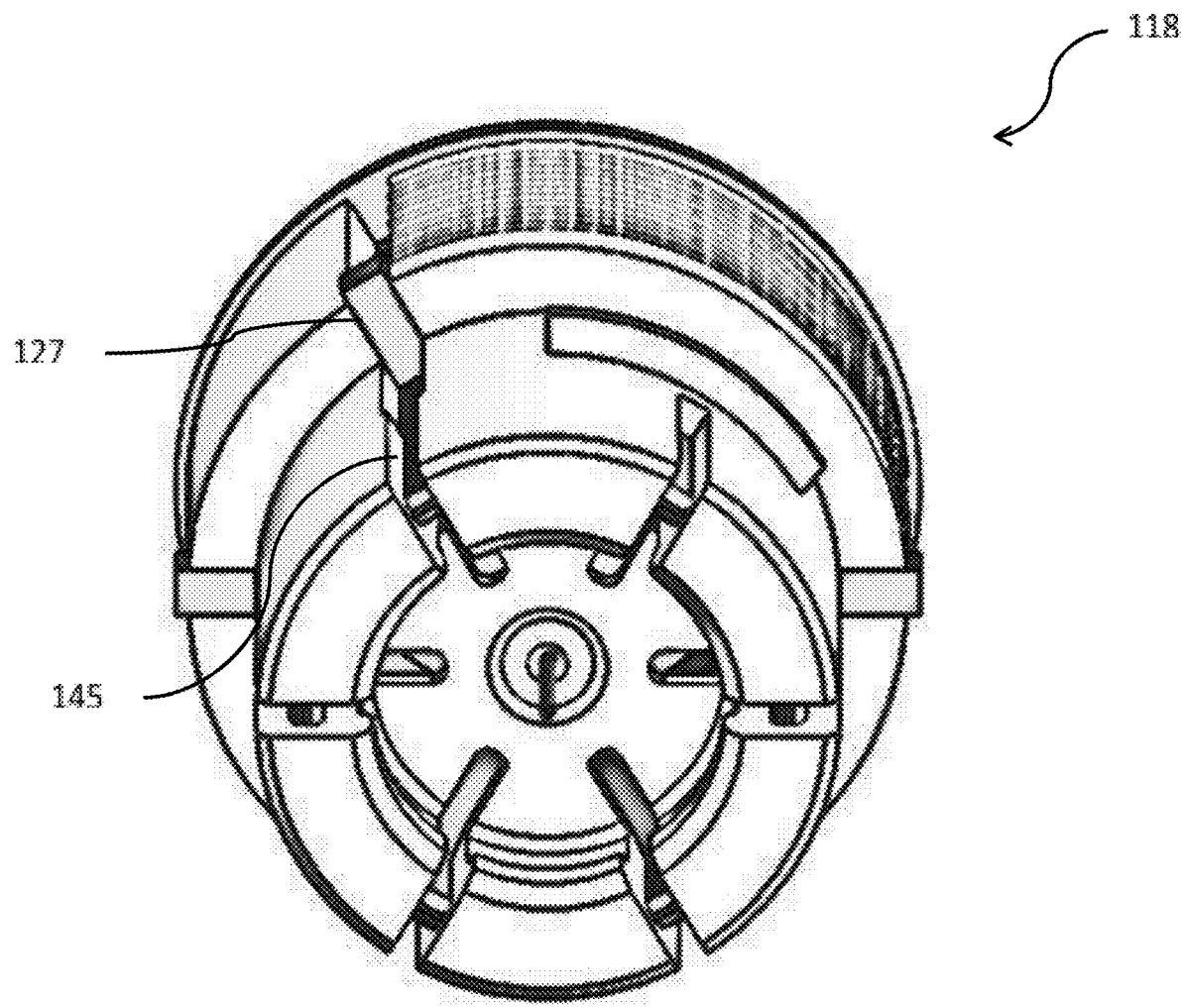

FIGS. 16-18 are perspective views that depict a connector 118 according to another embodiment. Connector 118 can include a body 124. Connector 118 can also include a plug 126, which can include a plurality of circumferentially spaced protruding members 127. The protruding members 127 can extend through longitudinal slots 145 defined by each adjacent pair of sections 144 of a proximal portion 136 of the body 124 of connector 118. The connector 118 can otherwise be the same as, or similar to, connector 18. The protruding members 127 can enhance the ability of connector 118 to prevent water ingress to a pump housing (e.g., 14).

Figure 19:
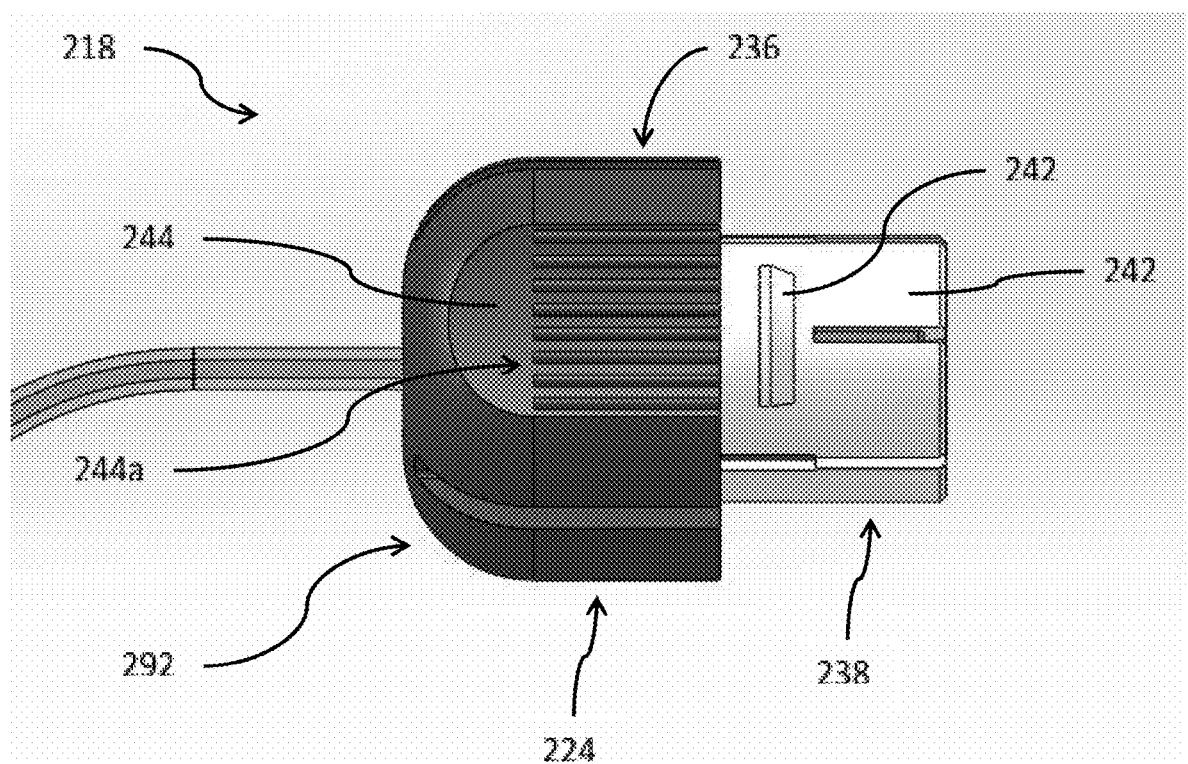
FIGS. 19-21 are elevational views depicting a connector of a medication delivery system, according to another embodiment.
Figure 20:
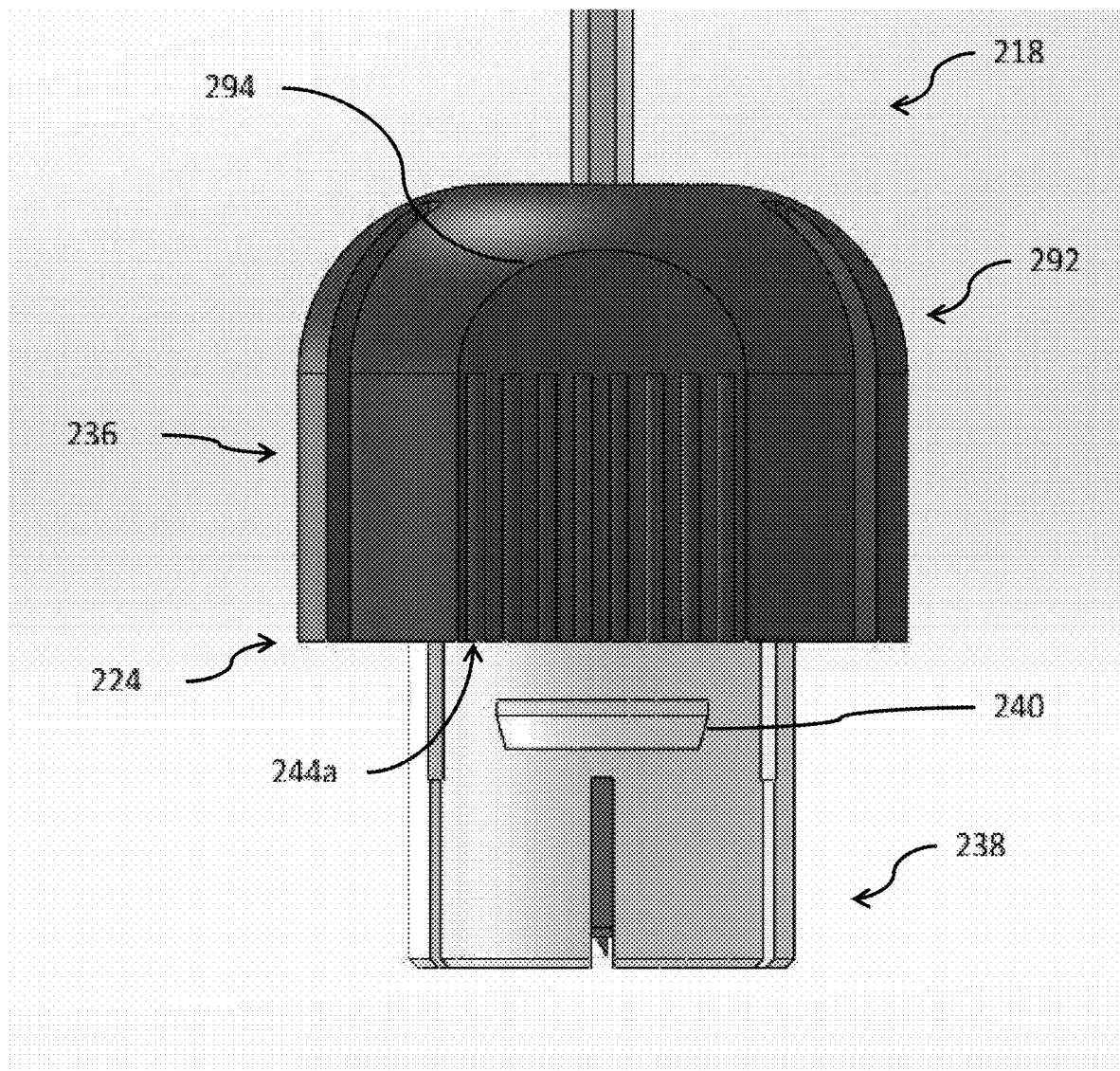
Figure 21:
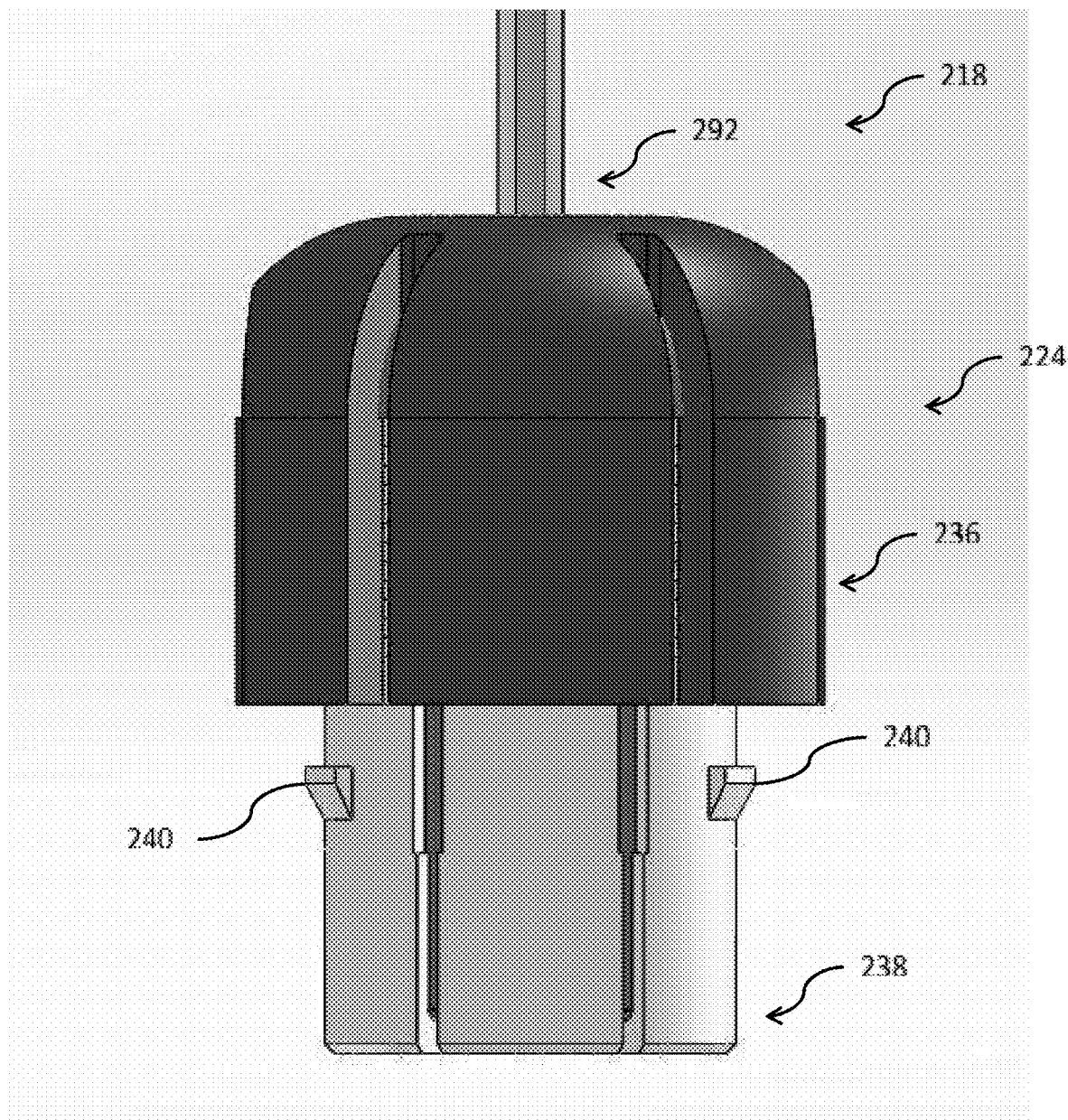

FIGS. 19-21 illustrate a connector 218 according to another embodiment. Connector 218 can include a body 224 and a plug (not shown). Connector 218 can also include a cover 292 which can abut a proximal portion 236 of body 224, and can at least substantially cover a proximal portion 236 of body 224. The proximal portion 236 can include a plurality of circumferentially spaced ribbed sections 244a and a like number of retention members 240, which can extend outwardly from respective ones of a plurality of circumferentially spaced flexible fingers 242 of the distal portion of 238. Connector 218 can include additional features, which can be the same as, or similar to, corresponding features of one or both of the connectors 18 and 118.

Unlike connectors 18 and 118, the cover 292 and the proximal portion 236 of body 224 can cooperate to define a plurality of concave indentations 294. Each of the ribbed sections 244a of the proximal portion 236 can be positioned in a respective one of the concave indentations 294. The concave indentations 294, in combination with the ribbed sections 244a, can facilitate grasping the connector 218 by a user. The plug of connector 218 can be attached to a reservoir (not shown) in a manner that is the same as, or similar to, that described for connector 18. Similarly, the combination of connector 218 and reservoir 216 can be releasably attached to a pump housing (e.g., 14) of a medication delivery system (e.g., 10) in a manner that is the same as, or similar to, that described for connector 18, reservoir 16, and pump housing 14 of the medication delivery system 10.

The use of connectors according to the inventive principles (e.g., 18, 118, 218) in medication delivery systems (e.g., 10) can provide several advantages relative to conventional connectors used in conventional medication delivery systems.

For example, conventional medication delivery systems that use mating, threaded male and female leurs to releasably couple a reservoir to a pump housing can be subject to leaks for at least the following reasons. The use of mating leurs inherently requires a high degree of user skill and dexterity to ensure proper engagement of the leurs to prevent insulin leakage. This can be problematic for diabetics who can have impaired dexterity due to their diabetes disease.

If the engagement of the mating leurs is too loose, the seal between the mating conical surfaces of the leurs can be lost, which can cause insulin leakage, resulting in an inadequate supply of insulin to the patient, which can have deleterious effects. Additionally, if the user applies excessive torque to the leurs, one of both of the leurs can crack, which can cause an insulin leak. Insulin leakage between the mating leurs can also occur if one of the leurs "backs off" of the other one of the leurs due to extended operation of the medication delivery system.

Similarly, leaks can occur in conventional systems that include a conventional connector having threads or cam surfaces that engage mating surfaces of another connector or a pump housing, if the engagement of the mating surfaces is loosened due to extended operation of the medication delivery system.

The attachment of connectors according to the inventive principles (e.g., 18, 118, and 218) to a pump housing (e.g., 14) can be achieved without any mating threads or cam surfaces, and without any rotation of the connectors, which can prevent the insulin leakage of the conventional connectors described above and can prevent the resulting delivery of an inadequate amount of insulin to the user.

The audible click resulting from the snap action engagement of the retention members according to the inventive principles (e.g., 40), with a pump housing (e.g., 14), can alert the user to the proper releasable attachment of the connector (e.g., 18) to the pump housing (e.g., 14). Additionally, the ribbed sections (e.g., 44a) of a connector (e.g., 18) according to the inventive principles, can help a user to grasp the connector, which can be particularly advantageous to a diabetic having impaired dexterity.

In some instances, conventional medication delivery systems which utilize two mating threaded connectors or two mating connectors having cam surfaces, or a mating connector and a pump housing, can result in delivery of an unwanted bolus of insulin to a person, which can produce significantly adverse effects for the person. This can occur if the respective threaded engagement is compromised as a result of one of the connectors rotating away from the other connector or the pump housing due to extended operation of the medication delivery system. When this occurs, a plunger positioned within a reservoir of the respective system can be spaced apart from a piston of an insulin pump, which is used to engage and move the plunger to force insulin out of the reservoir. This spacing can be an air pocket which can cause an inadequate delivery of basal insulin to the user over a period of time, which is not desirable. The insulin pump is programmed to continuously provide basal insulin to the user. Accordingly, after a period of time, the pump can move the piston into engagement with the plunger to resume dispensing insulin from the cartridge. After this occurs, an unwanted bolus of insulin can be dispensed from the reservoir if the user notices that the connector has "backed off", and tightens the connector again.

Use of the connectors according to the inventive principles can avoid an unwanted delivery of a bolus of insulin to the patient, since the connector (e.g., 18) and the attached reservoir (e.g., 16) can be releasably attached to a pump housing (e.g., 14) without the use of mating threads or mating cam surfaces, and without rotation of the connector (e.g., 18), so that the connector (e.g., 18) does not move away from the pump housing (e.g., 14) due to the extended operation of the medication delivery system (e.g., 10).

Use of the connectors according to the inventive principles (e.g., 18, 118, 218) can avoid an improper administration of other medications that can be dispensed by system 10, as compared to conventional systems subject to the problems discussed above.

It is to be understood that the embodiments and arrangements set forth herein are not limited in their application to the details of construction and arrangement of the components set forth in the description and illustrated in the drawings. Rather, the description and the drawings provide examples of the embodiments envisioned, but the invention is not limited to the specific embodiments. The embodiments disclosed herein are further capable of other embodiments and of being practiced and carried out in various ways, including various combinations and sub-combinations that may not have been explicitly disclosed. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the invention be regarded as including such equivalent constructions.

We claim:

1. A medical delivery system comprising;
a medical reservoir having a connector end and a reduction in circumference proximal to said connector end;
a housing with a connector aperture in it, said connector aperture being sized to allow insertion of said reservoir; and,
a connector for connecting said reservoir to said housing, said connector comprising a a central stem, a plurality of flexible fingers, and at least one retention member;
said central stem having a distal end, a proximal end, and a passage from its distal end to its proximal end;
each of said flexible fingers having a distal end and a proximal end, and being oriented parallel to said central stem, being arranged radially about said central stem, and being attached to said distal end of said central stem intermediate of said distal end and proximal end of each said flexible finger;
said distal ends of said fingers forming a reservoir aperture aligned with said passage, said reservoir aperture sized to receive said connector end of said reservoir;
said plurality of flexible fingers in combination defining a first outer circumference proximal to said distal ends of said flexible fingers, said first outer circumference being sized to insert into said connector aperture;
said at least one retention member being located on said first outer circumference, each of the retention members movable between a first, outward position and a second, inward position; wherein,
each of the retention members is forced toward the respective second inward position as said distal ends of said flexible fingers are inserted through said connector aperture, each of the retention members moving to the first outward position after passing through said connector aperture and resisting removal of said connector from said connector aperture.

2. The medical delivery system of claim 1, wherein;
said at least one retention member comprises a plurality of retention members spaced radially around said first outer circumference.

3. The medical delivery system of claim 1, wherein;
said at least one retention member produces an audible clicking sounds as it moves from the second, inward position to the first, outward position.

4. The medical delivery system of claim 1, wherein;
said connector aperture is round and said connector can rotate while inserted in said connector aperture.

5. The medical delivery system of claim 1, wherein;
said connector end of said reservoir snaps into said reservoir aperture.

6. The medical delivery system of claim 1, wherein;
each of the at least one retention members are movable from said first outward position to said second inward position by compressing said flexible fingers inwardly.

7. The medical delivery system of claim 1, wherein;
said proximal ends of said flexible fingers form a plug aperture concentric with said proximal end of said central stem, and said connector further comprises;
a plug, said plug having a distal portion and a proximal portion, said distal portion having a stem aperture, said stem aperture sized to receive said proximal end of said central stem, and said proximal portion having a tube aperture aligned with said stem aperture; wherein;
said distal portion of said plug inserts into said plug aperture and said proximal end of said central stem inserts into said stem aperture of said plug.

8. The medical delivery system of claim 1, wherein;
said connector end of said reservoir comprises a septum.

9. A medication delivery system comprising:
a connector comprising a body and at least one retention member extending outwardly from the body;
a reservoir attached to the connector and configured to retain a medication; and
a pump comprising a pump housing, the pump housing defining an aperture that is configured to permit the reservoir and a distal portion of the body to pass therethrough; wherein,
the connector is releasably coupled with the pump housing;
each of the retention members is movable between a first, outward position and a second, inward position; wherein,
each of the retention members is forced toward the respective second inward position as the distal portion of the body is inserted through the aperture defined by said pump housing, each of the retention members moving to the first outward position after passing through the aperture;
each of the retention members is engaged with the pump housing and prevents the connector and reservoir from moving proximally relative to the pump; and
each of the retention members creates an audible clicking sound as it moves from the second, inward position to the first, outward position;
the distal portion of the body comprises a plurality of flexible fingers, the flexible fingers being circumferentially spaced from one another;
the at least one retention member comprises a plurality of retention members, the retention members being circumferentially spaced from one another; and
each of the retention members extends outwardly from a respective one of the flexible fingers.

10. The medical delivery system of claim 9, wherein;
said aperture is round and said connector can rotate while inserted in said aperture.

11. A connector for a medication delivery system, the connector comprising:
a body comprising a proximal portion and a distal portion integral with the proximal portion; and at least one retention member extending outwardly from the distal portion of the body; wherein, each of the at least one retention member is movable from a first outward position to a second inward position by compressing the proximal portion of the body radially inwardly, the distal portion of the body comprises a plurality of flexible fingers, the flexible fingers being circumferentially spaced from one another;

the at least one retention member comprises a plurality of retention members, the retention members being circumferentially spaced from one another; and each of the retention members extends outwardly from a respective one of the flexible fingers.

12. The connector of claim 11, wherein:

the proximal portion of the body comprises a plurality of circumferentially extending and circumferentially spaced sections, each of the sections of the proximal portion being aligned with a respective one of the flexible fingers of the distal portion; and inward compression of any one of the sections of the proximal portion causes the aligned one of the flexible fingers of the distal portion to move inwardly.

13. The connector of claim 12, wherein;

the plurality of circumferentially extending and circumferentially spaced sections of the proximal portion comprise a plurality of ribbed sections, each of the ribbed sections being aligned with a respective one of the retention members.

14. The connector of claim 11, further comprising:

a plug, the plug comprising a cap and a shaft integral with the plug; wherein the body defines an interior chamber; and the shaft of the plug is disposed within the interior chamber, and the cap of the plug covers the interior chamber.

15. The connector of claim 14, wherein:

said body and plug are of unitary construction.

* * * * *